United States Patent
Funayama et al.

(10) Patent No.: US 9,121,818 B2
(45) Date of Patent: Sep. 1, 2015

(54) MOVABLE BODY SPECTRUM MEASURING APPARATUS AND MOVABLE BODY SPECTRUM MEASURING METHOD

(75) Inventors: Ryuji Funayama, Yokohama (JP); Kenji Sasaki, Gotemba (JP); Jun Sato, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 693 days.

(21) Appl. No.: 13/383,595

(22) PCT Filed: Jul. 30, 2010

(86) PCT No.: PCT/JP2010/062960
§ 371 (c)(1),
(2), (4) Date: Jan. 12, 2012

(87) PCT Pub. No.: WO2012/014327
PCT Pub. Date: Feb. 2, 2012

(65) Prior Publication Data
US 2012/0194817 A1  Aug. 2, 2012

(51) Int. Cl.
*G01J 3/46* (2006.01)
*G06F 11/30* (2006.01)
(Continued)

(52) U.S. Cl.
CPC ............... *G01N 21/31* (2013.01); *G01J 3/027* (2013.01); *G01J 3/2823* (2013.01)

(58) Field of Classification Search
CPC ................. G01J 3/18; G01J 3/14; G01J 3/36
USPC ............................ 356/402; 702/182–185, 188
See application file for complete search history.

(56) References Cited

U.S. PATENT DOCUMENTS 7,522,291 B2 * 4/2009 Hays et al. ..................... 356/519
7,564,539 B2 * 7/2009 Caldwell et al. ............. 356/28.5
(Continued)

FOREIGN PATENT DOCUMENTS

CN  102449448 A  5/2012
JP  2000 251052  9/2000
(Continued)

OTHER PUBLICATIONS

Kojima, H., et al., "A GA-based Band Selection Algorithm for Hyperspectral Image Classification," Journal of the Remote Sensing Society of Japan, vol. 25, No. 1, pp. 1-12, (Mar. 31, 2005) (with English abstract).

(Continued)

*Primary Examiner* — Tarifur Chowdhury
*Assistant Examiner* — Sunghee Y Gray
(74) *Attorney, Agent, or Firm* — Oblon, McClelland, Maier & Neustadt, L.L.P.

(57) ABSTRACT

A movable body spectrum measuring apparatus includes a spectrum sensor mounted in a movable body to measure spectrum data containing information including wavelength information and optical intensity information of a measuring object, a processor mounted in the movable body to discriminate the measuring object by processing the measured spectrum data, and a signal transmission path for transmitting the measured spectrum data from the spectrum sensor to the processor. The movable body spectrum measuring apparatus further includes a data transfer device which acquires reconfigured spectrum data by reconfiguring the measured spectrum data so that selected information as predetermined information is selected from the information contained in the measured spectrum data. The data transfer device transfers the reconfigured spectrum data to the processor via the signal transmission path.

13 Claims, 8 Drawing Sheets

(51) Int. Cl.
  *G06F 11/00* (2006.01)
  *G01N 21/31* (2006.01)
  *G01J 3/02* (2006.01)
  *G01J 3/28* (2006.01)

(56) References Cited

U.S. PATENT DOCUMENTS

| | | |
|---|---|---|
| 2005/0177307 A1 | 8/2005 | Greenfeld et al. |
| 2005/0189503 A1* | 9/2005 | Jamieson et al. .......... 250/559.4 |
| 2006/0262984 A1 | 11/2006 | Marcellin et al. |
| 2007/0129853 A1 | 6/2007 | Greenfeld et al. |
| 2008/0059080 A1* | 3/2008 | Greiner et al. .................. 702/33 |
| 2008/0147253 A1* | 6/2008 | Breed ................................ 701/3 |
| 2008/0211912 A1 | 9/2008 | Greenfeld et al. |
| 2012/0188545 A1 | 7/2012 | Funayama et al. |

FOREIGN PATENT DOCUMENTS

| | | |
|---|---|---|
| JP | 2005 77347 | 3/2005 |
| JP | 2005 528280 | 9/2005 |
| JP | 2006 145362 | 6/2006 |
| JP | 2008 26998 | 2/2008 |
| JP | 2008 541664 | 11/2008 |
| JP | 2010 210355 | 9/2010 |
| WO | 2010 137173 | 12/2010 |

OTHER PUBLICATIONS

International Search Report Issued Nov. 2, 2010 in PCT/JP10/62960 Filed Jul. 30, 2010.
International Preliminary Report on Patentability Issued Feb. 5, 2013 in PCT/JP10/062960 Filed Jul. 30, 2010.

* cited by examiner

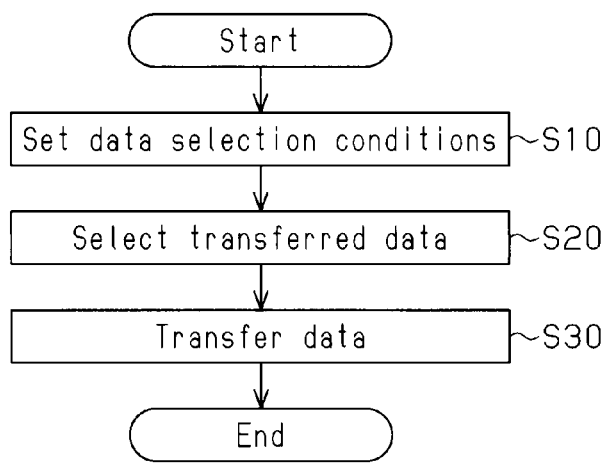
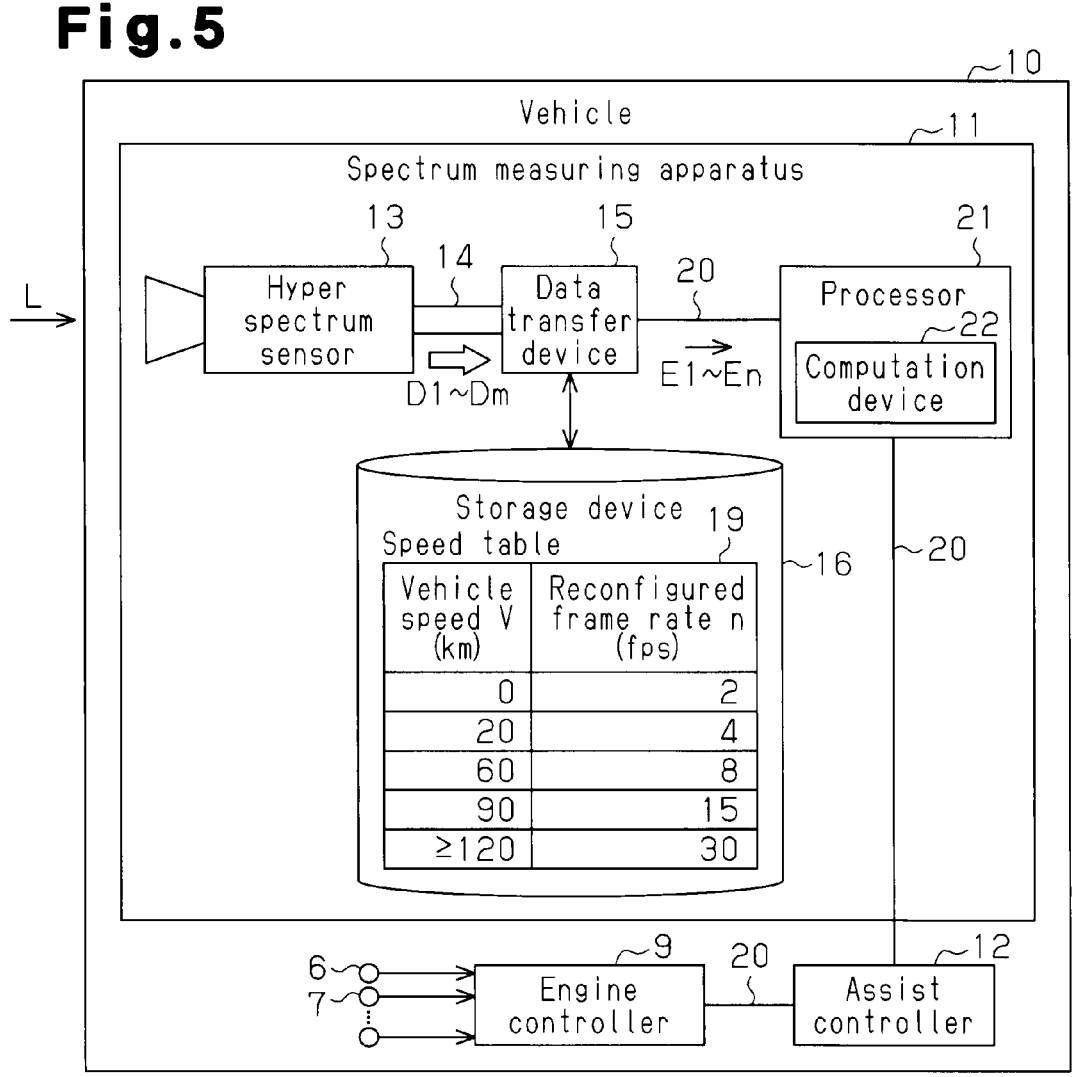

37 High resolution, low frame rate
36 Moderate resolution, moderate frame rate
35 Low resolution, high frame rate

MOVABLE BODY SPECTRUM MEASURING APPARATUS AND MOVABLE BODY SPECTRUM MEASURING METHOD

FIELD Of THE DISCLOSURE

The present invention relates to a movable body spectrum measuring apparatus having a spectrum sensor mounted in a movable body such as a vehicle, particularly an automobile, to measure spectrum data of a measuring object, and a movable body spectrum measuring method, and in particular, improvement of transfer process of spectrum data.

BACKGROUND OF THE DISCLOSURE

A spectrum measuring apparatuses, commercialization of which has been considered in recent years, recognizes a measuring object existing in ambient environment by using a spectrum sensor for measuring multi-spectrum data including a non-visible light region. When the spectrum measuring apparatus supplies information about a measuring object to a drive assistance device commercialized for vehicles such as automobiles, the drive assistance device can recognize pedestrians and other vehicles present in the surrounding traffic environment of the vehicle. Then, the drive assistance device can assist driving operation and decision making for the driver.

From the viewpoint of improving the accuracy of recognizing a measuring object (sensing target), it is desired that both spatial resolution and wavelength resolution of spectrum data measured by such spectrum measuring apparatus be high, or fine. However, when both spatial resolution and wavelength resolution are high, the amount of spectrum data may excessively increase. That is, to transfer a large amount of spectrum data, the spectrum measuring apparatus has to have a high data transfer capability and a high data processing capability. Particularly, since the spectrum measuring apparatus mounted in a movable body such as an automobile is strictly restricted in terms of various factors such as design and costs, it is not necessarily practical to achieve a high data transfer capability and a high data processing capability.

For example, a spectrum measuring apparatus described in Patent Document 1 switches between multi-spectrum observation for roughly setting wavelength resolution in place of finely setting spatial resolution and hyper-spectrum observation for roughly setting spatial resolution in place of finely setting wavelength resolution.

In the document, the spectrum measuring apparatus sets the wavelength resolution and spatial resolution to values corresponding to multi-spectrum observation or values corresponding to hyper-spectrum observation, for example, by binning of collectively read data for each pixel received by a detector formed of a two-dimensional CCD in a vertical or horizontal direction. Such switching between multi-spectrum observation and hyper-spectrum observation actually changes the amount of spectrum data. That is, the amount of spectrum data observed by the spectrum measuring apparatus is changed as necessary and the amount of spectrum data read by the detector is reduced as necessary.

PRIOR ART DOCUMENT

Patent Document

Patent Document 1: Japanese Laid-Open Patent Publication No. 2006-145362

SUMMARY OF THE INVENTION

Problems that the Invention is to Solve

However, to suppress the amount of the spectrum data while flexibly responding to various measuring objects and necessary measuring accuracy, only such switching between multi-spectrum observation and hyper spectrum observation as described in Patent Document 1 cannot necessarily ensure practical real-time operation.

An objective of the present invention is to provide a movable body spectrum measuring apparatus and a movable body spectrum measuring method that enables suitable real-time processing of data taken by a spectrum sensor while maintaining discrimination accuracy of a measuring object by a highly versatile spectrum sensor mounted in the movable body such as a vehicle.

Means for Solving the Problems

To achieve the foregoing objective, the present invention provides a movable body spectrum measuring apparatus that includes a spectrum sensor, a processor, a signal transmission path, and a data transfer device. The spectrum sensor is mounted in a movable body to measure spectrum data containing information including wavelength information and optical intensity information of a measuring object. The processor is mounted in the movable body to discriminate the measuring object by processing the measured spectrum data. The signal transmission path is used for transmitting the measured spectrum data from the spectrum sensor to the processor. The data transfer device acquires reconfigured spectrum data by reconfiguring the measured spectrum data such that selected information as predetermined information is selected from information contained in the measured spectrum data. The data transfer device transfers the reconfigured spectrum data to the processor through the signal transmission path.

With such a configuration, the data transfer device reduces information contained in measured spectrum data to only selected information and transfers reconfigured spectrum data after reduction to a processor. Thus, the amount of data flowing through a signal transmission path, that is, a communication line is reduced and the amount of spectrum data processed by the processor is also reduced. Thus, the spectrum sensor may be a high-performance hyper spectrum sensor. That is, even when the spectrum sensor acquires spectrum data containing a large amount of information, the amount of data transferred from the spectrum sensor to the processor is reduced to be an appropriate amount. Accordingly, transfer delay in the signal transmission path and processing delay in the processor are eliminated. As a result, the spectrum measuring apparatus can achieve recognition processing in real time while keeping a high recognition accuracy of the measuring object by the spectrum sensor.

In this manner, the spectrum measuring apparatus reduces the amount of measured spectrum data acquired by the spectrum sensor. Thus, in selecting the spectrum sensor used for the spectrum measuring apparatus, there is no need to suppress the capability of the spectrum sensor to be low. That is, there is no need to suppress the upper limit of the amount of measured spectrum data detected by the spectrum sensor to be low. Consequently, the flexibility in selecting the spectrum sensor is increased. That is, the versatile spectrum sensor can be employed for the spectrum measuring apparatus.

The selected information is preferably wavelength band information as a part of the wavelength information contained in the measured spectrum data.

With such a configuration, the data transfer device generates reconfigured spectrum data on the basis of wavelength band information as a part of the wavelength information acquired by the spectrum sensor. Thus, the amount of the reconfigured spectrum data transferred by the data transfer device is reduced more reliably than the amount of the measured spectrum data.

The part of the wavelength information is preferably the wavelength information necessary for discrimination of the measuring object.

With such a configuration, the data transfer device reconfigures the measured spectrum data on the basis of the wavelength band information as a part of the wavelength information, which is necessary for discrimination of a measuring object. Thus, the amount of the reconfigured spectrum data transferred by the data transfer device is reduced more reliably than the amount of the measured spectrum data while keeping the recognition accuracy of the measuring object.

The part of the wavelength information is preferably the wavelength information contained in ambient light in surroundings around the movable body.

With such a configuration, the data transfer device generates the reconfigured spectrum data on the basis of the wavelength band information as a part of the wavelength information, which is contained in the ambient light in the surroundings of the movable body. Thus, the wavelength information about wavelengths that are not contained in the ambient light, the wavelength information about wavelengths having low intensity and the optical intensity information corresponding to the above-mentioned wavelength information are eliminated from the measured spectrum data. The data transfer device selects only the wavelength information of light having high intensity in the ambient light and the optical intensity information corresponding to the wavelength information. Thus, the amount of the reconfigured spectrum data is reduced more reliably than the amount of the measured spectrum data. Since the wavelength information contained in the ambient light contains the wavelength information about light having high optical intensity according to the measuring object, the processor can suitably recognize the measuring object on the basis of the reconfigured spectrum data.

The selected information is preferably a part of the optical intensity information contained in the measured spectrum data.

With such a configuration, the data transfer device generates the reconfigured spectrum data on the basis of a part of the optical intensity information in the measured spectrum data. In other words, the reconfigured spectrum data is generated based on the density of the optical intensity information. Thus, the amount of the reconfigured spectrum data transferred by the data transfer device is reduced more reliably than the amount of the measured spectrum data.

The measured spectrum data may correspond to each of a plurality of spectrum images over time. The selected information may be information about the measured spectrum data corresponding to a partial period in a plurality of pieces of the measured spectrum data.

With such a configuration, the data transfer device generates the reconfigured spectrum data on the basis of the measured spectrum data corresponding to only a partial period in the measured spectrum data. Thus, the amount of the reconfigured spectrum data transferred by the data transfer device is reduced more reliably than the amount of the measured spectrum data.

The data transfer device may be configured to acquire the reconfigured spectrum data by extracting and excluding wavelength information having insignificant optical intensity information from information contained in the measured spectrum data.

With such a configuration, the wavelength information having an insignificant value such as a saturated or unchanged value of the optical intensity information is excluded from the reconfigured spectrum data. Thus, the amount of the transferred spectrum data is reduced.

The data transfer device may set a transfer maximum value as a maximum value of data amount transferable to the processor. The data transfer device may limit the amount of selected information such that the amount of the reconfigured spectrum data is equal to or smaller than the transfer maximum value.

With such a configuration, the data transfer device can limit the amount of the reconfigured spectrum data so as not to exceed data transfer capability of the signal transmission path, that is, the communication line and so as not to exceed data processing capability of the processor. Thus, transfer delay and processing delay of the reconfigured spectrum data are suppressed. That is, real-time performance in the recognition processing of the measuring object by the spectrum measuring apparatus is ensured.

Priority may be set to each of a plurality of the measuring objects. The data transfer device may be configured to determine the selected information on the basis of the priority.

With such a configuration, the data transfer device generates the reconfigured spectrum data according to the priority. Thus, the processor can reliably recognize the measuring object having a high priority in the real-time processing.

The movable body includes a movable body state acquiring unit for acquiring a movable body state as a state of the movable body. The data transfer device may be configured to determine the selected information according to the movable body state.

With such a configuration, the data transfer device can change wavelength interval of the wavelength information, density of the optical intensity information and acquisition time of the spectrum data to generate the reconfigured spectrum data according to the movable body state such as vehicle speed and a steering operation. Thus, the processor can recognize the measuring object on the basis of the proper reconfigured spectrum data corresponding to the movable body state. Thus, the measuring object is suitably discriminated.

The processor may be configured to set the selected information. The processor may be configured to make a request to the data transfer device on the basis of a recognition result of the measuring object. The data transfer device may be configured to determine the selected information according to the request.

With such a configuration, the data transfer device can generate the reconfigured spectrum data by adjusting the wavelength interval of the wavelength information, the density of the optical intensity information and the acquisition time of the spectrum data on the basis of feedback from the processor. For example, when estimating that the occurrence ratio of a certain measuring object is high by processing of the reconfigured spectrum data, the processor sets the priority of the measuring object, that is, an object of high occurrence ratio to be high and changes the selected information so as to correspond to the object of high occurrence ratio. By using the tuned selected information, the data transfer device generates the reconfigured spectrum data so as to contain information effective to recognition of the object of high occurrence ratio. Thus, the processor can flexibly recognize the measuring object with a narrowed target. That is, recognition performance of the measuring object can be improved.

There is an object of high occurrence ratio having a higher occurrence ratio than other measuring objects among a plurality of measuring objects. Data amount reduced by reconfiguration from the measured spectrum data to the reconfigured spectrum data is referred to as data reduced amount. The selected information may be set such that the data reduced amount of the object of high occurrence ratio is smaller than that of the other measuring objects.

With such a configuration, the processor can discriminate an object of high occurrence ratio even in the case where data amount is large. Thus, the discrimination accuracy of the measuring object is kept high.

The measured spectrum data is used to generate a spectrum image. The selected information corresponding to a central region of the spectrum image may be set to be different from the selected information corresponding to a peripheral region of the spectrum image.

With such a configuration, the data transfer device selects different information independently in the central region and the peripheral region of the spectrum image. For example, the measuring object existing in the central region of the spectrum image is away from the movable body and thus, looks small and its relative speed is low. Thus, the data transfer device sets frame rate to be low in place of finely setting the wavelength information and the optical intensity information of the selected information corresponding to the central region of the spectrum image. Thus, an increase in the data amount can be prevented. In contrast, a measuring object existing in the peripheral region of the spectrum image is near the movable body and thus, looks large and its relative speed is high. Thus, the data transfer device roughly sets the wavelength information and the optical intensity information in place of setting the frame rate of the selected information corresponding to the peripheral region of the spectrum image to be high. Thus, an increase in the data amount can be prevented. As a result, the data transfer device can finely discriminate the measuring object according to the location of the spectrum image.

The processor may be configured to set the selected information. A specified one of the measuring object is referred to as a specific measuring object. The processor may be configured to set the selected information so as to exclude the measured spectrum data corresponding to the existence of the specific measuring object when recognizing that the specific measuring object exists in a measuring scope of the spectrum sensor.

With such a configuration, when the processor already has recognized a specific measuring object by use of, for example, another means such as map information and radar, the data transfer device can exclude the spectrum data corresponding to the specific measuring object from the reconfigured spectrum data. Thus, the amount of the reconfigured spectrum data is reliably reduced.

In order to generate the reconfigured spectrum data, the data transfer device may represents the wavelength information corresponding to wavelength in a certain range as representative wavelength information, and calculate representative optical intensity information on the basis of optical intensity information corresponding to the wavelength information.

With such a configuration, the wavelength information included in the certain wavelength range is replaced with one representative wavelength information, and the optical intensity information corresponding to the certain wavelength range is replaced with one piece of representative optical intensity information. Thus, the amount of the reconfigured spectrum data is reduced in due course. For example, the data transfer device replaces the wavelength information included in the wavelength range of 550 nm to 650 nm with the representative wavelength information of 600 nm according to a superimposition method. Further, the data transfer device replaces the optical intensity information corresponding to the wavelength range of 550 nm to 650 nm with one piece of representative optical intensity information of 600 nm by convolution or averaging. Thus, the amount of the reconfigured spectrum data is reliably reduced.

To achieve the foregoing objective, the present invention provides a movable body spectrum measuring method that includes: measuring spectrum data containing information including wavelength information and optical intensity information of a measuring object by a spectrum sensor mounted in a movable body; discriminating the measuring object by processing the measured spectrum data by a processor mounted in the movable body; transmitting the measured spectrum data from the spectrum sensor to the processor via a signal transmission path. The transmitting includes: acquiring reconfigured spectrum data by reconfiguring the measured spectrum data such that selected information as predetermined information is selected from the information included in the measured spectrum data; and transferring the reconfigured spectrum data to the processor via the signal transmission path.

According to this method, the reconfigured spectrum data obtained by reducing information contained in the measured spectrum data to only the selected information is transferred to the processor. Thus, the amount of the data flowing through the signal transmission path, that is, the communication line is reduced, and the amount of the spectrum data processed by the processor is also reduced. Thus, the spectrum sensor may be a high-performance hyper spectrum sensor. That is, when the spectrum sensor acquires the measured spectrum data containing a large amount of information, the data transferred from the spectrum sensor to the processor is reduced to an appropriate data amount. In addition, transfer delay in the signal transmission path and processing delay in the processor are eliminated. As a result, the movable body spectrum measuring method enables the spectrum measuring apparatus to execute the recognition processing in real time while keeping the recognition accuracy of the measuring object by the spectrum sensor high.

As described above, the spectrum measuring method reduces the amount of the measured spectrum data obtained by the spectrum sensor. Thus, according to the spectrum measuring method, in selecting the spectrum sensor used for the spectrum measuring apparatus, there is no need to suppress the capability of the spectrum sensor to be low. That is, there is no need to suppress the upper limit of the amount of the measured spectrum data detected by the spectrum sensor to be low. Thus, the flexibility in selecting the spectrum sensor is improved.

BRIEF DESCRIPTION OF DRAWINGS

FIG. 4 is a flowchart showing a procedure of generating reconfigured spectrum data by the spectrum measuring apparatus in FIG. 1;

FIG. 5 is a block diagram showing schematic configuration of a movable body spectrum measuring apparatus in accordance with a second embodiment of the present invention having a speed table representing relationship between vehicle speed and frame rate;

DETAILED DESCRIPTION OF THE PREFERRED EMBODIMENTS (First Embodiment)

Figure 1:
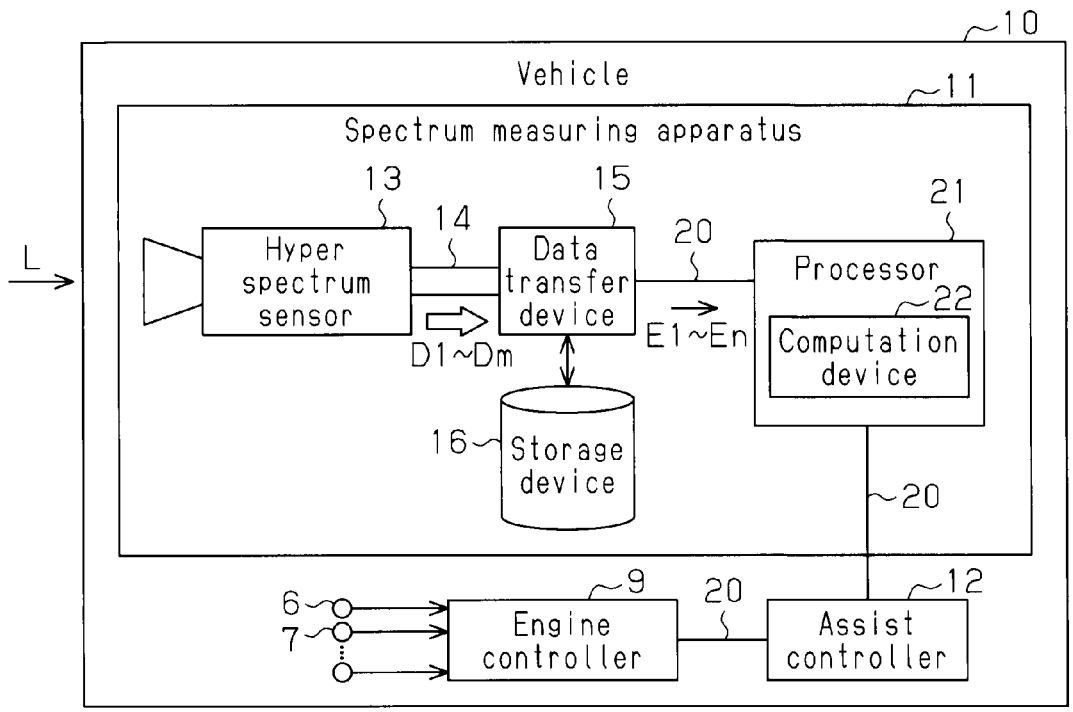
FIG. 1 is a block diagram showing a schematic configuration of a movable body spectrum measuring apparatus in accordance with a first embodiment of the present invention.

FIGS. 1 to 4 show a spectrum measuring apparatus 11 as a movable body spectrum measuring apparatus in accordance with a first embodiment of the present invention. FIG. 1 is a block diagram schematically showing the system configuration of the spectrum measuring apparatus 11.

As shown in FIG. 1, a vehicle 10 as a movable body includes various sensors as a movable body state acquiring unit, such as a vehicle speed sensor 6 for detecting the vehicle speed V and a steering angle sensor 7 for detecting the steering angle, and a hyper spectrum sensor 13. The hyper spectrum sensor 13 constitutes a part of the spectrum measuring apparatus 11. The vehicle 10 further includes various controllers such as an engine controller 9 for controlling the engine (not shown) and an assist controller 12 for assisting the driver's driving operation. Information from the vehicle speed sensor 6 and the steering angle sensor 7 is input from the engine controller 9 and the assist controller 12 directly or indirectly. A processor 21 is connected to the assist controller 12 and the assist controller 12 is connected to the engine controller 9 via an on-vehicle network 20.

The spectrum measuring apparatus 11 is configured to processes observation light L from outside of the vehicle 10, which is formed from light information including visible light and non-visible light, thereby recognizing a measuring object and to output recognition information about the measuring object to the assist controller 12. The assist controller 12 transmits the recognition information to another controller such as the engine controller 9. The assist controller 12 is configured to perform drive assistance required for each measuring object. The assist controller 12 transmits vehicle information as information about the vehicle 10, which is transmitted directly from the vehicle speed sensor 6 and the steering angle sensor 7 or indirectly via the engine controller 9, to the spectrum measuring apparatus 11. That is, the vehicle speed sensor 6, the steering angle sensor 7 and the engine controller 9 constitute a vehicle information acquiring unit for acquiring the vehicle information representing the state of the vehicle 10. The vehicle information includes the ON/OFF state of a headlight of the vehicle 10, the operational state of a direction indicator and the vehicle speed V.

As shown in FIG. 1, the spectrum measuring apparatus 11 includes the hyper spectrum sensor 13 for detecting spectrum data D1 to Dm from the observation light L as light from the measuring object, a large-capacity communication circuit 14 for transporting the measured spectrum data D1 to Dm, and a data transfer device 15 for generating reconfigured spectrum data E1 to En from the measured spectrum data D1 to Dm. The letters m and n each are an integer representing a frame rate and will be described below in detail.

The spectrum measuring apparatus 11 further includes the processor 21 for executing the recognition processing of recognizing a measuring object by using the reconfigured spectrum data E1 to En. The data transfer device 15 is connected to the processor 21 via the on-vehicle network 20. The large-capacity communication circuit 14 can perform communication having larger capacity than the on-vehicle network 20, but is shorter. The large-capacity communication circuit 14 and the part of the on-vehicle network 20 between the data transfer device 15 and the processor 21 constitutes the signal transmission path between the hyper spectrum sensor 13 and the processor 21. The hyper spectrum sensor 13 processes the observation light L as light formed of visible light and non-visible light, thereby generating spectrum images separated into a plurality of wavelength bands.

Figure 2:
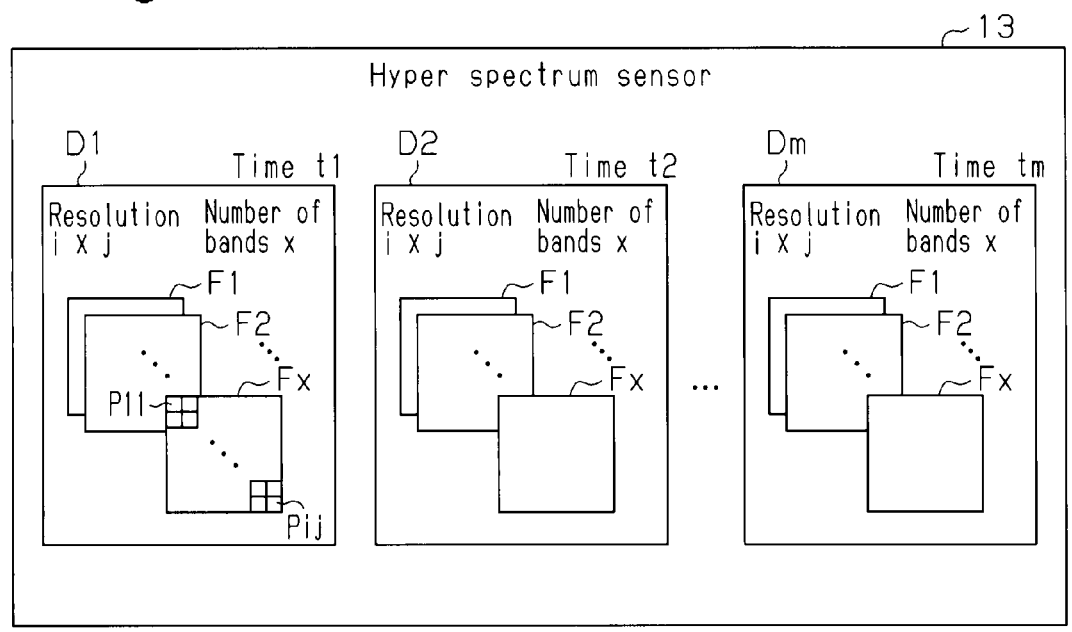
FIG. 2 is a schematic view of spectrum data measured by the spectrum sensor in FIG. 1.

FIG. 2 shows the measured spectrum data D1 to Dm as the spectrum images acquired by the hyper spectrum sensor 13 in detail. The measured spectrum data D1 to Dm correspond to time t1 to tm of the frame rate of the hyper spectrum sensor 13, respectively. Given that the frame rate m=20 fps (frame per second), the hyper spectrum sensor 13 measures 20 measured spectrum data D1 to Dm per second. The measured spectrum data D1 to Dm correspond to the spectrum images changing over time, which is acquired by the hyper spectrum sensor 13, respectively.

Given that the number of measured bands x of the wavelength of the hyper spectrum sensor 13 is 150, the measured spectrum data D1 has 150 single-wavelength images F1 to Fx. For example, in the range of the measured wavelength band of the hyper spectrum sensor 13, 400 nm (nanometer) is set as a measurement start wavelength, 2635 nm is set as a measurement end wavelength and a wavelength resolution f is selected to be 15 nm. In this case, the number of measured bands x of the hyper spectrum sensor 13 of 150 is obtained by dividing the measured wavelength band [2635 nm to 400 nm] by the wavelength resolution f of 15 nm. Like the measured spectrum data D1 at the time t1, other measured spectrum data D2, Dm at the time t2 and tm each has 150 single-wavelength images F1 to Fx. That is, the hyper spectrum sensor 13 measures the frame rate f×the number of measured bands x=20×150=3000 single-wavelength images F1 to Fx per second. As described above, the single-wavelength images F1 to Fx each are an image corresponding to each wavelength included in the measured wavelength band measured by the hyper spectrum sensor 13. In other words, the measured spectrum data D1 is configured of the single-wavelength images F1 to Fx of the number of measured bands x as the number obtained by dividing the measured wavelength band by the wavelength resolution f.

Given that the spatial resolution, that is, the resolution of the hyper spectrum sensor 13 is 640×480, one single-wavelength image F1 has i×j single-wavelength pixels P11 to Pij in a matrix. A horizontal resolution i is 640 and a vertical resolution j is 480. Since one single-wavelength pixel P11 has one single-wavelength optical intensity information p11, one single-wavelength image F1 contains 640×480 single-wavelength optical intensity information p11 to pij.

The frame rate m, the number of measured bands x and the spatial resolution i×j are not limited to the above-mentioned values and are optionally set according to specifications of the hyper spectrum sensor 13.

Thus, the measured spectrum data D1 to Dm as the spectrum images each has the wavelength information (the number of bands m) as information representing wavelengths configuring the separated wavelength band, and the single-wavelength optical intensity information p11 to pij as information representing the optical intensity of the observation light L for each wavelength in the wavelength band. The measured spectrum data D1 to Dm as the spectrum images each further has the plurality of single-wavelength images F1 to Fx as images observed according to each wavelength in the wavelength band. The single-wavelength images F1 to Fx are images observed according to each wavelength included in the measured wavelength band of the hyper spectrum sensor 13.

The hyper spectrum sensor 13 has a detection plane (not shown) configured of a plurality of imaging elements such as CCD or CMOS for detecting the optical intensity information. The imaging elements configuring the detection plane detect the respective single-wavelength optical intensity information p11 to pij corresponding to the single-wavelength pixels P11 to Pij configuring the spectrum image. That is, the plurality of single-wavelength pixels P11 to Pij configuring the measured spectrum data D1 to Dm has the single-wavelength optical intensity information p11 to pij as individual spectrum data corresponding to the measured wavelength band. In other words, the single-wavelength images F1 to Fx has the plurality of single-wavelength pixels P11 to Pij and the single-wavelength optical intensity information p11 to pij corresponding to the plurality of single-wavelength pixels P11 to Pij, respectively. Thus, for example, the single-wavelength optical intensity information p11 of the single-wavelength pixels P11 configures the single-pixel optical intensity information.

The large-capacity communication circuit 14 shown in FIG. 1, as described above, transfers the measured spectrum data D1 to Dm configured of 3000 single-wavelength images F1 to Fx to the data transfer device 15 per second. The large-capacity communication circuit 14 is a communication circuit such as a data bus that can transfer a large amount of data at high speed. That is, the large-capacity communication circuit 14 can successively transfer the measured spectrum data D1 to Dm obtained by the hyper spectrum sensor 13 to the data transfer device 15 without causing congestion on the way, that is, causing delay. The large-capacity communication circuit 14 is a versatile inexpensive high-speed and large-capacity communication circuit having high reliability and can be implemented by the publicly known communication circuit. The communication distance of the large-capacity communication circuit 14 is limited to a short distance, for example, a few to a dozen of centimeters at the longest, in order to keep communication performance. Especially when used in environment with a lot of electrical noises, such as the vehicle, the communication distance of the large-capacity communication circuit 14 is limited to a shorter distance.

The data transfer device 15 mainly includes a microcomputer having a computation device and a storage device. The storage device previously stores a program used for data selection processing for generating the reconfigured spectrum data E1 to En and various setting values required for the data selection processing therein. The data transfer device 15 includes a temporary storage device (not shown) for temporarily storing the plurality of measured spectrum data D1 to Dm and reconfigured spectrum data E1 to En.

Figure 3:
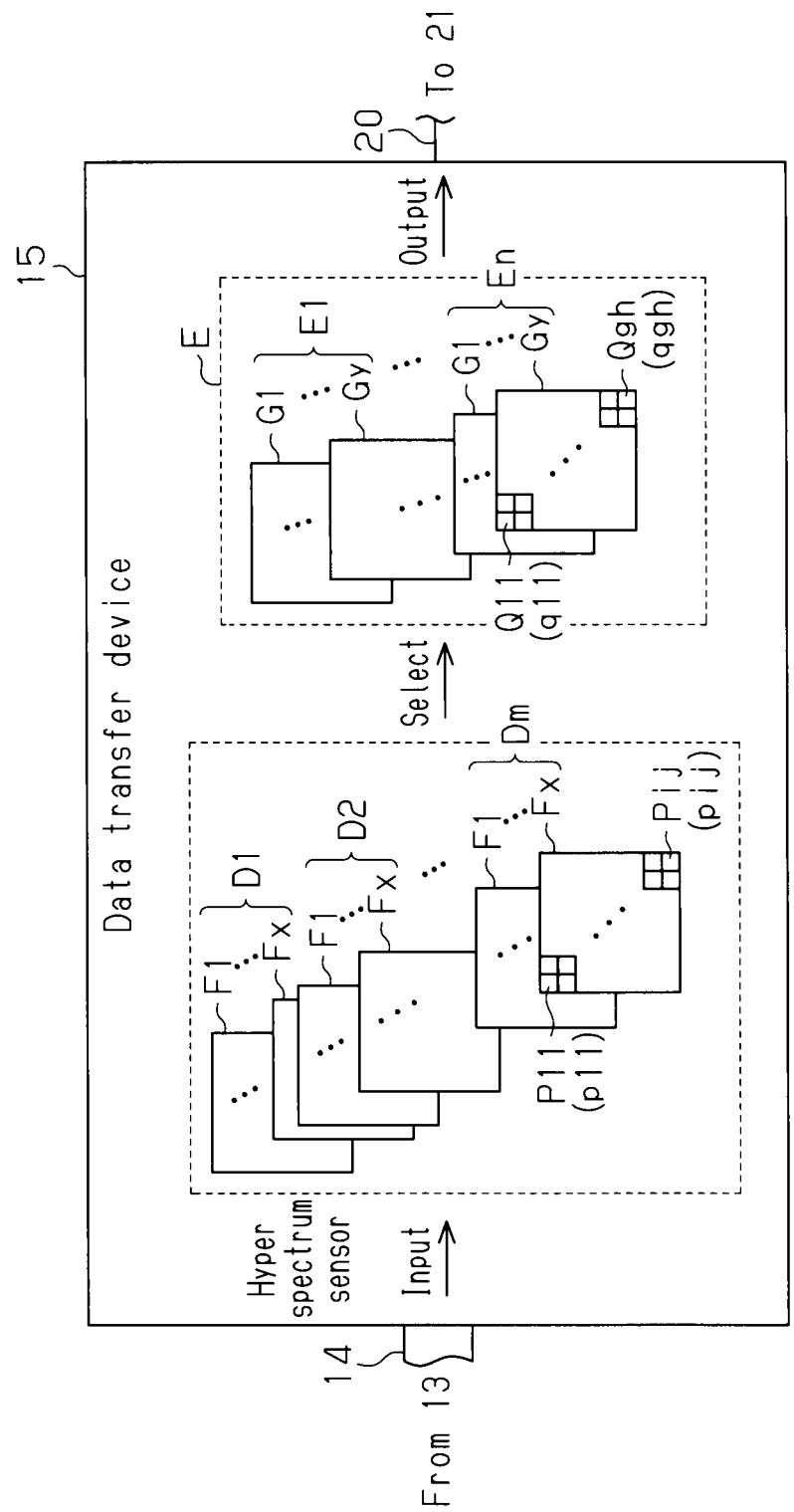
FIG. 3 is a schematic view showing a mode in which the data transfer device in FIG. 1 selects spectrum data information.

FIG. 3 shows the reconfigured spectrum data E1 to En generated by reconfiguration of the measured spectrum data D1 to Dm by the data transfer device 15. That is, the data transfer device 15 generates the reconfigured spectrum data E1 to En by reducing and reconfiguring the measured spectrum data D1 to Dm by thinning or convolution of a part of information contained in the measured spectrum data D1 to Dm. The data transfer device 15 outputs the reconfigured spectrum data E1 to En to the processor 21 via the on-vehicle network 20.

The letter n represents the frame rate of the reconfigured spectrum data E1 to En and the letter y represents the number of reconfigured bands. For example, the reconfigured spectrum data E1 is the spectrum image configured of a plurality of, that is, y reconfigured single-wavelength images G1 to Gy. The reconfigured single-wavelength images G1 to Gy are images containing information selected from the measured spectrum data D1 to Dm, respectively, according to the data selection processing. For example, the reconfigured single-wavelength image G1 has reconfigured single-wavelength pixels Q11 to Qgh in a matrix. That is, g represents horizontal resolution and h represents vertical resolution of reconfigured spatial resolution. Reconfigured optical intensity information q11 to qgh as reconfigured single-wavelength optical intensity information corresponding to the reconfigured single-wavelength pixels Q11 to Qgh, respectively, is acquired.

A storage device 16 in FIG. 1 is all or part of a storage area of the publicly known storage device. The storage device 16 stores one or more data selection conditions as the predetermined information, that is, the selected information, which is used in the data selection processing by the data transfer device 15 therein. The data transfer device 15 acquires the data selection conditions used in the data selection processing from the storage device 16. The storage device 16 in this embodiment stores the plurality of data selection conditions that are different from each other in an information reducing mode and the reduced amount of information therein. The data transfer device 15 in this embodiment selects a suitable data selection condition from the storage device 16 on the basis of specifications of the on-vehicle network 20 and the processor 21, and executes the data selection processing according to the selected data selection condition.

A predetermined condition representing the predetermined information, that is, the selected information, which is selected from the measured spectrum data D1 to Dm by the data transfer device 15 to generate the reconfigured spectrum data E1 to En, is at least one of, for example, a "frame rate change condition", a "wavelength resolution change condition" and a "resolution change condition". The "frame rate change condition" serves to reduce the number of the measured spectrum data D1 to Dm, the "wavelength resolution change condition" serves to reduce the number of the single-wavelength images F1 to Fx and the "resolution change condition" serves to reduce the number of the single-wavelength pixels P11 to Pij. The data selection conditions are not limited to these.

[Frame Rate Change Condition]

The frame rate change condition is used to select a part of the measured spectrum data D1 to Dm as the spectrum image and generate the reconfigured spectrum data E1 to En. That is, the frame rate n of the reconfigured spectrum data E1 to En is set to be smaller than the frame rate m of the measured spectrum data D1 to Dm. The value m is larger than the value n (m>n).

For example, the data transfer device 15 selects only D1 as the selected information from the measured spectrum data D1 to D5 and deletes D2, D3, D4 and D5. That is, only the measured spectrum data D1 accounting for one fifth is selected. In summary, the data transfer device 15 sets the reconfigured spectrum data E1=D1, E2=D6, E3=D11, E4=D16, . . . . That is, the reconfigured frame rate n is m/5, that is, 4 (n=m/5=4).

In this case, even with the constant number of measured bands x=the number of reconfigured bands y=150, the number of the reconfigured single-wavelength images G1 to Gy of the reconfigured spectrum data E1 to En is n×y=4×150=600. Thus, the information amount of the reconfigured spectrum data E1 to En is one fifth of the 3000 single-wavelength images F1 to Fx.

[Wavelength Resolution Change Condition]

The wavelength resolution change condition is used to select a part from the single-wavelength images F1 to Fx and generate the reconfigured single-wavelength images G1 to Gy. That is, the number of reconfigured bands y as the number of bands of the reconfigured single-wavelength images G1 to Gy is set to be smaller than the number of measured bands x as the number of bands of the single-wavelength images F1 to Fx. x is larger than y. Based on the reconfigured single-wavelength images G1 to Gy, the reconfigured spectrum data E1 to En is generated. That is, the wavelength resolution of the reconfigured spectrum data E1 to En is set to be rougher, that is, lower than the wavelength resolution of the measured spectrum data D1 to Dm. For example, the data transfer device 15 selects only F1 as a part of the wavelength information from the single-wavelength images F1 to F10 and deletes remaining F2 to F9. That is, only the single-wavelength images F1 accounting for one tenth is selected. In summary, the data transfer device 15 sets the reconfigured single-wavelength images G1=F1, G2=F11, G3=F21, . . . , G15=F141. That is, the number of reconfigured bands y is 15.

In this case, even with the constant number of frames m=n=20, the number of the reconfigured single-wavelength images G1 to Gy of the reconfigured spectrum data E1 to En is n×y=20×15=300. Thus, the information amount of the reconfigured spectrum data E1 to En is one tenth of the 3000 single-wavelength images F1 to Fx of the measured spectrum data D1 to Dm.

[Resolution Change Condition]

The resolution change condition is used to select a part from the single-wavelength pixels P11 to Pij and generate the reconfigured single-wavelength pixels Q11 to Qgh. In other words, the reconfigured optical intensity information q11 to qgh corresponding to a part of the single-wavelength pixels P11 to Pij is generated from the single-wavelength optical intensity information p11 to pij corresponding to the single-wavelength pixels P11 to Pij, respectively. Thus, the resolution of the reconfigured single-wavelength images G1 to Gy is rougher, that is, lower than the resolution of the single-wavelength images F1 to Fx. For example, the data transfer device 15 selects only p11 from the 16 single-wavelength optical intensity information p11 to p14, p21 to p24, p31 to p34 and p41 to p44 in 4 by 4 matrix, and deletes the remaining 15 p12 to p14, p21 to p24, p31 to p34 and p41 to p44. That is, data transfer device 15 sets the reconfigured optical intensity information q11=p11, q12=p15, q13=p19, . . . , q21=p51, q22=p55, q23=p59, . . . . In other words, pixels accounting for one fourth in the horizontal direction and pixels accounting for one fourth in the vertical direction are selected.

Thus, reconfigured spatial resolution g×h=(640/4)×(480/4)=160×120. That is, the information amount of the reconfigured optical intensity information q11 to qgh is one sixteenth of 640×480 single-wavelength optical intensity information p11 to pij.

The data transfer device 15 selects at least one of these data selection conditions and executes the data selection processing on the basis of the selected data selection condition.

As a result, the information amount of the reconfigured spectrum data E1 to En created by the data transfer device 15 is reliably reduced from the information amount output from the hyper spectrum sensor 13. In other words, the data amount based on the information contained in the reconfigured spectrum data E1 to En per device time is reduced from the amount of the measured spectrum data D1 to Dm per device time.

The on-vehicle network 20 shown in FIGS. 1 and 3 is, for example, an on-vehicle local controller area network (CAN) and a general communication line that can ensure some communication distance, for example, a few to a dozen of meters. In other words, since the on-vehicle network 20 has high flexibility in the wiring constituting the communication line, the distance between devices that communicate with each other can be ensured. Any device other than the data transfer device 15 and the processor 21 may be connected to the on-vehicle network 20. In other words, the on-vehicle network 20 enables high flexibility in arrangement for the data transfer device 15 and the processor 21 in the vehicle 10.

Although the on-vehicle network 20 has high flexibility in the wiring and device connection, when the amount of communication data becomes large, collision of communication data and communication latency are caused, thereby lowering the communication efficiency and limiting the amount of transferable data. In this embodiment, the amount of data that can be communicated by the on-vehicle network 20 is smaller than, that is, for example, a fraction to a couple of hundredth of the amount of data that can be transferred by the large-capacity communication circuit 14. The data transfer device 15 outputs the reconfigured spectrum data E1 to En, the amount of which is reduced from the amount of the measured spectrum data D1 to Dm, to the on-vehicle network 20 by reconfiguration. Consequently, the amount of data transferred from the data transfer device 15 to the on-vehicle network 20 can be reduced to the data amount that can be reliably transferred via the on-vehicle network 20. That is, the reconfigured spectrum data E1 to En can be reliably transferred to the processor 21 via the on-vehicle network 20.

The processor 21 shown in FIG. 1 mainly includes a microcomputer having a computation device 22 and a storage device. Since the processor 21 is connected to the data transfer device 15, the reconfigured spectrum data E1 to En output from the data transfer device 15 is input to the processor 21. The processor 21 recognizes the measuring object by executing discrimination processing of the measuring object on the basis of the input reconfigured spectrum data E1 to En. Since the processor 21 recognizes the measuring object according to a publicly known method, in this embodiment, detailed description of the processor 21 for recognizing the measuring object and the recognition processing for recognizing the measuring object is omitted for convenience.

The processor 21 executes the discrimination processing of the measuring object on the basis of the input reconfigured spectrum data E1 to En. The processor 21, for example, compares the measured spectrum image with the spectrum image of the measuring object, which is previously stored in the storage device (not shown), and determines whether or not these spectrum images match each other, and recognizes the measuring object on the basis of the determination result. Such comparison of spectrum images usually requires much processing such as processing of selecting a comparison region and processing of comparing spectrum images by sequentially updating the measuring object until the measuring object is identified in the selected comparison region, and the processing requires many arithmetic computations by the computation device 22.

In contrast, measurement of the spectrum image by the hyper spectrum sensor 13 takes only a short time. As a result, when the processor 21 executes the recognition processing of all spectrum images taken by the hyper spectrum sensor 13, the computation device 22 that performs arithmetic computations on the recognition processing needs to have high performance. However, the on-board processor 21 (computation device 22) is necessarily subjected to various limitations in terms of design and costs. For this reason, when performances of the processor 21 and the computation device 22 included in the processor 21 are merely enhanced, which possibly causes problems in versatility, cost and maintenance performance.

In this embodiment, the data transfer device 15 reduces the amount of the reconfigured spectrum data E1 to En transferred to the processor 21 to an amount that can be reliably recognized by the processor 21, so that the reconfigured spectrum data E1 to En can be reliably processed by the processor 21 in real time.

In this manner, the processor 21 recognizes the measuring object while ensuring real-time performance by the recognition processing of the computation device 22. The processor 21 also uses information about the recognized measuring object and transmits the information about the recognized measuring object to the assist controller 12 as an external device of the spectrum measuring apparatus 11.

FIG. 4 is a flowchart showing the procedure for the data selection processing by the data transfer device 15. The data selection processing is successively executed in sync with measurement of the spectrum image by the hyper spectrum sensor 13.

When the data selection processing is started, in Step S10, the data transfer device 15 sets the data selection conditions. That is, the data transfer device 15 in this embodiment sets the transfer maximum value as the maximum value for the data amount that can be transferred to the on-vehicle network 20 on the basis of the transferable data amount defined for the on-vehicle network 20 or the data amount defined for the processor 21, which can be recognized in real time. In this embodiment, the transfer maximum value is previously set in the data transfer device 15 and the storage device 16. When the transfer maximum value is set, the data transfer device 15 acquires the data selection conditions for generating the reconfigured spectrum data E1 to En that does not exceed the transfer maximum value from the storage device 16. In Step S20, the data transfer device 15 selects information contained in the measured spectrum data D1 to Dm on the basis of the data selection conditions and reconfigures the selected information, thereby generating the reconfigured spectrum data E1 to En. Thus, the reconfigured spectrum data E1 to En with the reduced information amount, that is, data amount, is generated. In Step S30, the data transfer device 15 transfers the reconfigured spectrum data E1 to En to the processor 21.

As describe above, the data transfer device 15 sets the amount of the reconfigured spectrum data E1 to En so as not to exceed the data transfer capability of the on-vehicle network 20 and throughput of the processor 21. Thus, delay in transfer of the reconfigured spectrum data E1 to En by the on-vehicle network 20 and delay of the processor 21 on the basis of the reconfigured spectrum data E1 to En are prevented. Thus, the recognition processing of the measuring object on the basis of the spectrum image is reliably executed in real time.

In the above-mentioned Patent document 1, the spectrum measuring apparatus performing binning can variously change the data amount by optionally setting the wavelength resolution and the spatial resolution in reading of data from a detector. However, since the general detector is a part of the spectrum sensor, control of the detector itself can complicate design of the spectrum sensor or lower versatility and maintenance property of the spectrum sensor. In this connection, the data transfer device 15 in this embodiment reduces the amount of the measured spectrum data D1 to Dm output from the hyper spectrum sensor 13 without arranging the hyper spectrum sensor 13 itself. As a result, in this embodiment, the hyper spectrum sensor 13 having a high spectrum measuring capability in the as-is status can be used for the spectrum measuring apparatus 11.

As described above, the spectrum measuring apparatus 11 in accordance with the first embodiment in FIGS. 1 to 4 has the advantages listed as follows.

(1) The data transfer device 15 is configured to reduce information contained in the measured spectrum data D1 to Dm by selecting only the selected information as the predetermined information, and transfer the reconfigured spectrum data E1 to En as the reduced data to the processor 21. As a result, the amount of data flowing through the on-vehicle network 20 and the amount of the reconfigured spectrum data E1 to En to be processed by the processor 21 are reduced. Thus, even when the measured spectrum data D1 to Dm acquired by the high-performance hyper spectrum sensor 13 contains a large amount of information, the spectrum measuring apparatus 11 can reduce the amount of the measured spectrum data D1 to Dm to an appropriate amount and transfer the reduced reconfigured spectrum data E1 to En to the processor 21. As a result, transfer delay in the on-vehicle network 20 and processing delay in the processor 21 are eliminated. In other words, the spectrum measuring apparatus 11 can sufficiently execute the recognition processing in real time while keeping the recognition accuracy of the measuring object high by use of the hyper spectrum sensor 13.

(2) The measured spectrum data D1 to Dm output from the hyper spectrum sensor 13 is partially reduced. As a result, in adopting the hyper spectrum sensor 13, there is no need to consider whether or not the amount of the measured spectrum data D1 to Dm is too much with respect to the on-vehicle network 20 or exceeds the throughput of the processor 21. Thus, the flexibility in selecting the spectrum sensor is improved. That is, even the versatile spectrum sensor can be used for the spectrum measuring apparatus 11.

(3) The data transfer device 15 generates the reconfigured spectrum data E1 to En on the basis of the wavelength band information as a part of the wavelength information output from the hyper spectrum sensor 13, that is, the wavelength resolution change condition. Thus, the amount of the reconfigured spectrum data E1 to En transferred from the data transfer device 15 can be reliably reduced.

(4) The data transfer device 15 generates the reconfigured spectrum data E1 to En on the basis of a part of the optical intensity information output from the hyper spectrum sensor 13, that is, the resolution change condition, in other words, according to the resolution based on the density of the optical intensity information. Thus, the amount of the reconfigured spectrum data transferred from the data transfer device 15 is reliably reduced from the measured spectrum data.

(5) The data transfer device 15 generates the reconfigured spectrum data E1 to En on the basis of partial temporal information of the measured spectrum data D1 to Dm corresponding to the spectrum images output from the hyper spectrum sensor 13 over time, respectively. In other words, the reconfigured spectrum data E1 to En is generated from the measured spectrum data D1 to Dm according to the frame rate of the spectrum image taken over time, that is, the frame rate change condition. Thus, the amount of the reconfigured spectrum data E1 to En transferred from the data transfer device 15 can be reliably reduced.

(6) The data transfer device 15 sets the maximum value of the reconfigured spectrum data E1 to En to be equal to or smaller than a maximum capacity value of data amount that is determined depending on the data transfer capability of the on-vehicle network 20, that is, the signal transmission path or the communication line, and the data processing capability of the processor 21 and can be dealt with in real time. Thus, in transferring the reconfigured spectrum data E1 to En, delay in transfer of data and processing delay of data are suppressed and therefore, the real-time performance of the measuring object recognition processing by the spectrum measuring apparatus 11 is reliably improved.

(Second Embodiment)

Figure 6:
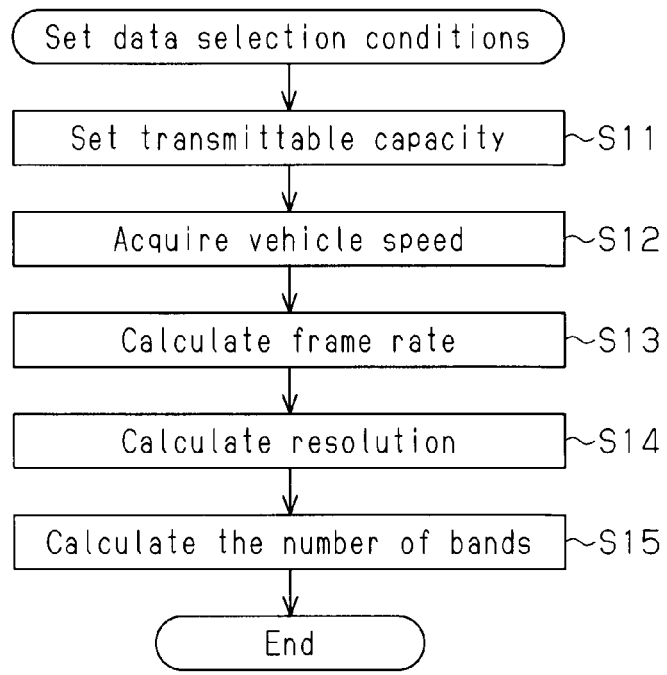
FIG. 6 is a flowchart showing a procedure for generating spectrum data by the movable body spectrum measuring apparatus in FIG. 5.

FIGS. 5 and 6 show the spectrum measuring apparatus 11 in accordance with a second embodiment of the present invention. As shown in FIG. 5, this embodiment is different from the first embodiment in that a speed table 19 for selecting the reconfigured frame rate n according to the vehicle speed V is included. Other configuration is similar and thus, the similar constituents are given the same reference numerals and description thereof is not repeated here. That is, the data selection conditions in this embodiment are not previously set and vary according to the vehicle speed V. Setting of the data selection conditions in the flowchart of FIG. 6 corresponds to details of Step S10 in FIG. 4.

As shown in FIG. 5, the speed table 19 sets the reconfigured frame rate n to 2 fps when the vehicle speed V is less than 20 km. Similarly, the speed table 19 sets the reconfigured frame rate n to 4 fps when the vehicle speed V is 20 km or more and less than 60 km, to 8 fps when the vehicle speed V is 60 km or more and less than 90 km, to 15 fps when the vehicle speed V is 90 km or more and less than 120 km and to 30 fps when the vehicle speed V is 120 km or more.

For example, a transmittable capacity ct as the transfer maximum value of the on-vehicle network 20 is expressed as n×y×g×h using the reconfigured frame rate n, the number of reconfigured bands y and reconfigured resolution g×h.

FIG. 6 is a flowchart showing a processing procedure for setting the data selection conditions by the spectrum measuring apparatus 11. As shown in FIG. 6, when setting of the data selection conditions is started, in Step S11, the data transfer device 15 sets an initial transmittable capacity ct0. The initial transmittable capacity ct0 is set based on information about the vehicle 10, which is newly acquired by the data transfer device 15. The newly acquired information about the vehicle 10 includes a recognition state of the measuring object and information acquired based on external environment of the vehicle, and the data transfer device 15 acquires the information from the processor 21 via the on-vehicle network 20. For example, the initial transmittable capacity ct0 may be set by the data transfer device 15 on the basis of the priority of the measuring object or limited information necessary for discriminating the measuring object. Further, for example, the initial transmittable capacity ct0 may be set by the data transfer device 15 on the basis of data amount that is acquired from the processor 21 and can be transferred via the on-vehicle network 20 on each occasion or data amount that can be processed by the processor 21 on each occasion. Expressing the initial value using a lower suffix "0", the initial transmittable capacity ct0 is n0×y0×g0×h0. For example, it is given that an initial reconfigured frame rate n0 is 10 fps, the initial number of reconfigured bands y0=20 (20 bands) and the initial reconfigured resolution g0×h0 is 320×240 (320×240 pixels).

In Step S12, the data transfer device 15 acquires the vehicle speed V from the assist controller 12 via the processor 21. In Step S13, the data transfer device 15 selects the reconfigured frame rate n by referring to the speed table 19 stored in the storage device 16.

In Step S14, the data transfer device 15 selects the new reconfigured resolution g1×h1. In Step S15, the data transfer device 15 calculates the new number of reconfigured bands y1. For example, when the reconfigured resolution g1×h1 is maintained to be a constant value g0×h0 irrespective of the vehicle speed V, the new number of reconfigured bands y1 is calculated according to an equation: $y1 = ct0/(g0 \times h0)/n1$. As a result, when the vehicle speed V is slow, the wavelength resolution is increased by increasing the number of reconfigured bands y1 in place of decreasing the reconfigured frame rate n1. Conversely, when the vehicle speed V is fast, in order to find the measuring object within a short time, the number of reconfigured bands y1 is decreased in place of increasing the reconfigured frame rate n1. When the new reconfigured frame rate n1, the new reconfigured resolution g1×h1 and the new number of reconfigured bands y1 are determined, the data transfer device 15 generates the reconfigured spectrum data E1 to En on the basis of the reconfigured frame rate n1, resolution m2 and the new number of bands b2. Then, the data transfer device 15 transmits the reconfigured spectrum data E1 to En to the processor 21 via the on-vehicle network 20.

In this manner, the second embodiment in FIGS. 5 and 6 can also obtain the same or similar advantages as those in the first embodiment as well as the following advantage.

(7) The data transfer device 15 changes the reconfigured frame rate n of the reconfigured spectrum data E1 to En according to the vehicle speed V. Thus, the processor 21 can recognize the measuring object in real time while keeping the recognition accuracy even with respect to a change in the vehicle speed V.

(Third Embodiment)

Figure 7:
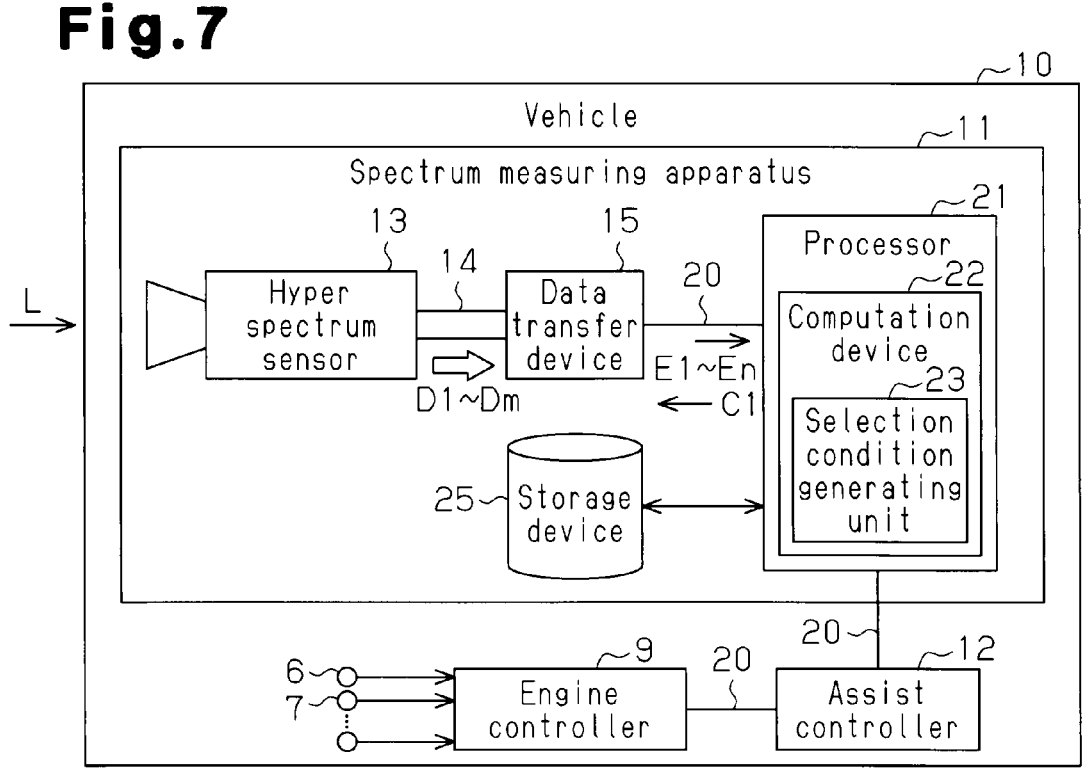
FIG. 7 is a block diagram showing schematic configuration of a movable body spectrum measuring apparatus in accordance with a third embodiment of the present invention.

FIG. 7 is a block diagram showing schematic configuration of the spectrum measuring apparatus 11 in accordance with a third embodiment of the present invention. This embodiment is different from the first embodiment in that the data transfer device 15 does not acquire the data selection conditions from the storage device 16 and the processor 21 sets a data selection condition C1 as the selected information to the data transfer device 15. The computation device 22 has a selection condition generating unit 23 for generating the data selection condition C1. Other configuration is similar and thus, same description as in the first embodiment is not repeated here.

As shown in FIG. 7, the processor 21 acquires various tables representing the priority of the measuring object from a storage device 25. The priority of the measuring object includes fixed priority previously determined for each measuring object, priority varying according to feedback of the current recognition state of the measuring object by the processor 21 and priority varying according to the state of the vehicle 10 and environment outside of the vehicle. The storage device 25 also stores wavelength information (wavelength band constituted of one or more pieces of wavelength information) necessary for discrimination of each measuring object therein. Further, the storage device 25 may also store wavelength information suitable for recognition of the measuring object according to light source spectrum of ambient light in day and night therein.

The selection condition generating unit 23 calculates the measuring object to be preferentially detected by referring to the priority of the measuring object, which is set in the storage device 25. The selection condition generating unit 23 also refers to the storage device 25 so as to reflect the current recognition state of the measuring object by the processor 21. Based on the calculated priority, the selection condition generating unit 23 generates the data selection condition C1 as the selected information suitable for detection of the measuring object by referring to the storage device 25, and outputs the data selection condition C1 to the data transfer device 15.

For example, when it is determined that a pedestrian, a car and the road surface should be preferentially detected at all times, the selection condition generating unit 23 may generate the data selection condition C1 for selecting information suitable for detection of the pedestrian, the automobile and the road surface. For example, when a pedestrian should be preferentially detected, for example, when a pedestrian should be preferentially detected since the pedestrian is not previously detected, the data selection condition C1 suitable for detection of the pedestrian may be generated and output to the data transfer device 15. For example, as the data selection condition C1, when no pedestrian is found in preprocessing, to quickly find a newly appearing pedestrian, the reconfigured frame rate n may be increased, while the reconfigured resolution g×h and the number of reconfigured bands y may be decreased. Alternatively, when the pedestrian is found in the previous processing, to discriminate the found pedestrian with high accuracy, the data selection condition C1 is set so as to set the wavelength resolution in front of and behind the wavelength corresponding to the pedestrian high to clarify the boundary between the pedestrian and the surrounding or to discriminate the attribute of the pedestrian.

The selection condition generating unit 23 may also generate the data selection condition C1 so that the wavelength information suitable for detection of the measuring object is set for day or night. For example, when detecting lighting of the headlight via the assist controller 12, the selection condition generating unit 23 generates the data selection condition C1 mainly including the wavelength information corresponding to a wavelength component contained in the headlight as a light source. When detecting night via the assist controller 12, the selection condition generating unit 23 generates the data selection condition C1 mainly including the wavelength information corresponding to a wavelength component of an illuminating lamp or a flood light.

Further, the selection condition generating unit 23 generates the data selection condition C1 suitable for detection of the measuring object according to the vehicle speed V and the steering angle that are acquired from the assist controller 12.

The selection condition generating unit 23 sets the data selection condition C1 thus generated to the data transfer device 15. The data transfer device 15 generates the reconfigured spectrum data E1 to En from the measured spectrum data D1 to Dm on the basis of the set data selection condition C1. Thus, the amount of the reconfigured spectrum data E1 to En is reliably reduced from the amount of the measured spectrum data D1 to Dm.

In this manner, the third embodiment in FIG. 7 can obtain the same or similar advantages as those in the first embodiment as well as following listed advantages.

(8) The processor 21 sets the data selection condition C1 and transmits the set data selection condition C1 to the data transfer device 15. Thus, the data transfer device 15 can generate the reconfigured spectrum data E1 to En on the basis of a detailed instruction according to the circumstances.

(9) The processor 21 can set the data selection condition C1 so as to be based on the wavelength band information as a part of the wavelength information, which is included in ambient light, that is, a light source in the surroundings of the movable body, in the wavelength information. Thus, the processor 21 can set the data selection condition C1 so as to eliminate the wavelength information about the wavelength that is not included in the ambient light, that is, the light source and the wavelength having a low intensity, and the optical intensity information corresponding to the wavelength information. Accordingly, since the data transfer device 15 can select only the wavelength information about the wavelength having a high intensity under the ambient light, that is, the light source, and the optical intensity information corresponding to the wavelength information, the amount of the reconfigured spectrum data E1 to En is reliably reduced. Moreover, since the reconfigured spectrum data E1 to En contains the wavelength information including the optical intensity varying according to the measuring object under the ambient light, the processor 21 can reliably execute the recognition processing even on the basis of the reconfigured spectrum data E1 to En with reduced amount.

(10) The selection condition generating unit 23 can set the data selection condition C1 as requested so as to perform feedback to the data transfer device 15 according to the recognition result of the measuring object by the processor 21. The selection condition generating unit 23 can change the data selection condition C1 on the basis of a wavelength interval of the wavelength information, the density of the optical intensity information and the acquisition time of the spectrum data. For example, according to the recognition result of the processor 21, when the priority is changed to measure the object of high occurrence ratio, which is expected to appear, the processor 21 can change the data selection condition C1 so as to capture the object of high occurrence ratio. As a result, data reconfiguring processing of the data transfer device 15 is improved so as to flexibly change and recognize the required measuring object. In turn, recognition performance of the measuring object is improved.

(Fourth Embodiment)

Figure 8:
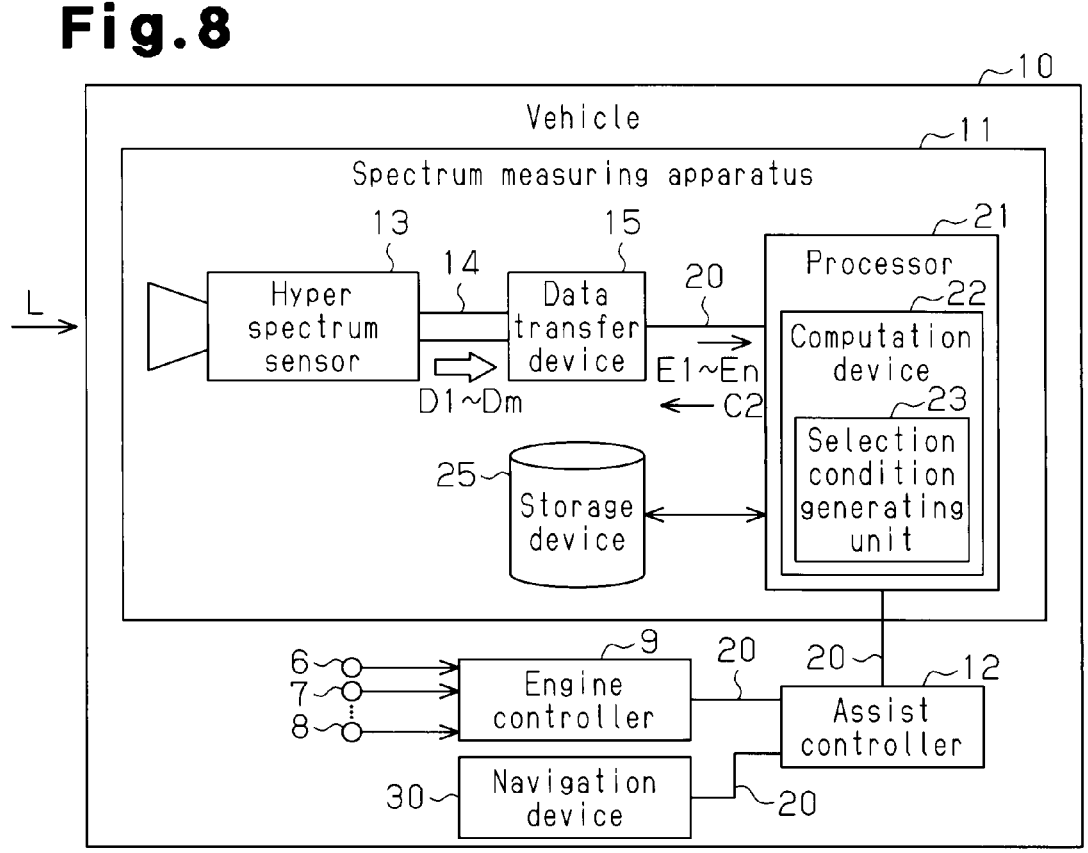
FIG. 8 is a block diagram showing schematic configuration of a movable body spectrum measuring apparatus in accordance with a fourth embodiment of the present invention.

FIG. 8 is a block diagram showing schematic configuration of the spectrum measuring apparatus 11 in accordance with the fourth embodiment of the present invention. This embodiment is different from the third embodiment in FIG. 7 in that a navigation device 30 as an extension of an environment information acquiring device is added. An optical sensor 8 is further provided.

As shown in FIG. 8, the navigation device 30 as a part of the environment information acquiring device is connected to the processor 21 via the assist controller 12. Alternatively, the navigation device 30 may be directly connected to the processor 21. The navigation device 30 is a device for acquiring information about the external environment of the vehicle 10, and for example, constitutes various environment acquiring devices for acquiring driving position of the vehicle 10 and day or night. The navigation device 30 transmits various types of environment information to the processor 21. By detecting location information of the vehicle 10, the navigation device 30 can detect characteristics of driving places such as an urban area, an expressway and a agricultural field, and transmit their positions on a map on a display panel to the driver. The navigation device 30 may determine day or night by means of a clock or an illuminometer. When acquiring position, the navigation device 30 may identify the position based on location information of GPS (Global Positioning System) or a combination of the location information and the map, or may acquire the position by communications using a system informing location information. Alternatively, the optical sensor 8 as a part of the environment information acquiring device may transmit another detection information about the ambient light and day or night to the processor 21 via the engine controller 9.

The storage device 25 sets various tables representing the priority of the measuring object therein. The priority of the measuring object, which is set according to the environment state acquired by the navigation device 30, is previously stored. For example, information about the higher priority of the measuring object frequently appearing due to characteristics of the current location and information about the lower priority of the measuring object that does not appear due to characteristics of the driving place are set. The storage device 25 also stores the wavelength information necessary for discriminating each measuring object therein.

The selection condition generating unit 23 calculates the measuring object to be preferentially detected by referring to the priority of the measuring object, which is set in the storage device 25 according to the environment information input from the navigation device 30. The selection condition generating unit 23 generates a data selection condition C2 on the basis of the calculated priority, and sets the data selection condition C2 to the data transfer device 15.

For example, when the navigation device 30 detects an urban area, the processor 21 may generate the data selection condition C2 that causes the data transfer device 15 to select information suitable for detection of a bicycle and a pedestrian. For example, when the navigation device 30 detects an expressway, the processor 21 may generate the data selection condition C2 that causes the data transfer device 15 to select information suitable for detection of automobile. Alternatively, the processor 21 may generate the data selection condition C2 that causes the data transfer device 15 to select information suitable for detection of the pedestrian who hardly appears in the expressway, but has a great impact. The selection condition generating unit 23 may generate the data selection condition C2 that causes the data transfer device 15 to select information suitable for detection of the measuring object for each of day and night.

For example, the selection condition generating unit 23 may generate the data selection condition C2 that causes the data transfer device 15 to select only the wavelength information corresponding to the light source spectrum observed or assumed by the optical sensor 8. Further, for example, the selection condition generating unit 23 may generate the data selection condition C2 to select wavelength information about light of red "R", green "G" or blue "B" according to request of image information for display on the display panel of the navigation device 30.

The selection condition generating unit 23 sets the data selection condition C2 thus generated to the data transfer device 15. The data transfer device 15 generates the reconfigured spectrum data E1 to En from the measured spectrum data D1 to Dm on the basis of the set data selection condition C2. Thus, the amount of the reconfigured spectrum data E1 to En is reliably reduced from the amount of the measured spectrum data D1 to Dm.

In this manner, a fourth embodiment in FIG. 8 can also obtain the same or similar advantages as those in the first and third embodiments as well as a following advantage.

(11) Since the processor 21 can discriminate the measuring object on the basis of the reconfigured spectrum data E1 to En reconfigured to have a larger amount of data, the discrimination accuracy of the spectrum measuring apparatus 11 is improved in due course.

(Fifth Embodiment)

Figure 9:
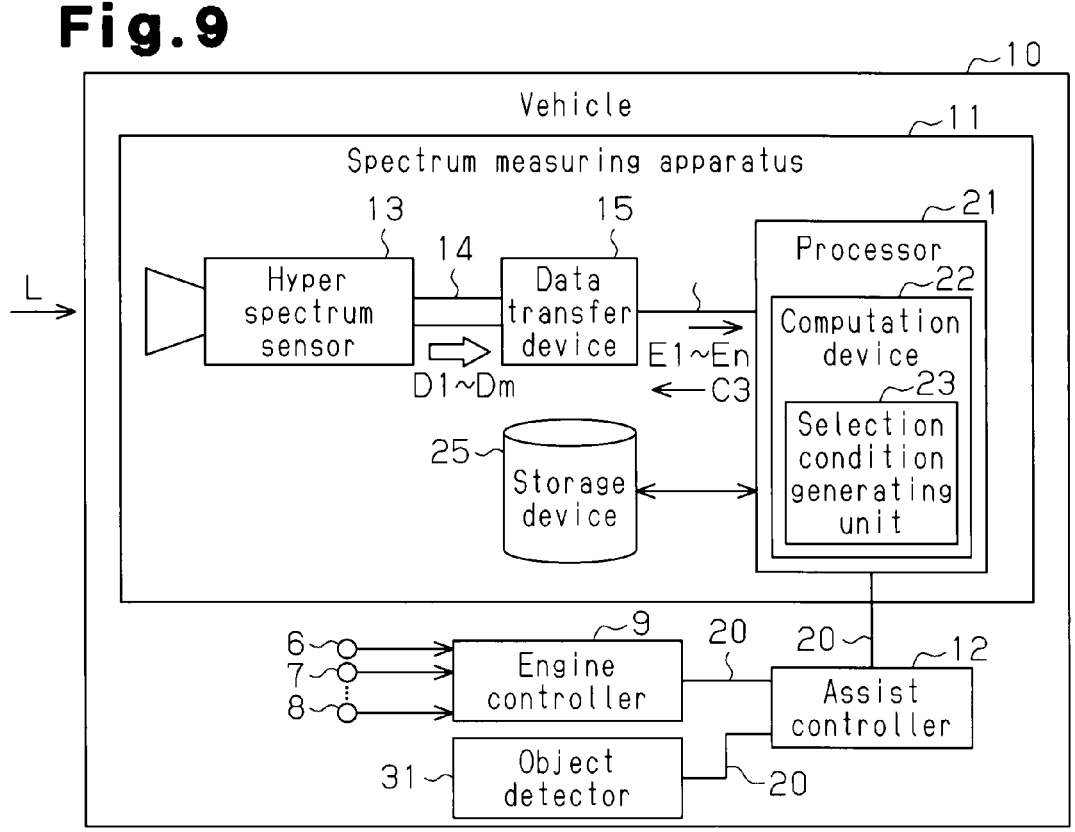
FIG. 9 is a block diagram showing schematic configuration of a movable body spectrum measuring apparatus in accordance with a fifth embodiment of the present invention.

FIG. 9 is a block diagram showing a schematic configuration for the spectrum measuring apparatus 11 in accordance with a fifth embodiment of the present invention. This embodiment is different from the third embodiment in FIG. 7 in that an object detector 31 such as a camera, radar or a laser measuring device is used.

As shown in FIG. 9, the object detector 31 is connected to the processor 21 via the assist controller 12. Alternatively, the object detector 31 may be directly connected to the processor 21. The object detector 31 detects a measuring object or a detecting object that exists in the external environment of the vehicle 10. For example, the object detector 31 is an information acquiring device for detecting a measuring object or the detecting object such as the vehicle driving in front, a structure and a building that surround the road to detect a measuring object or a detecting object on the basis of map information and location information. The object detector 31 transmits the detected detecting object to the processor 21. That is, the object detector 31 is a device for detecting the vehicle driving in front by image recognition based on an image taken by the camera, the radar or the laser. Further, the object detector 31 may be a navigation system for detecting the structure and the building that surround the road on the basis of the location information of the vehicle 10 and informing their positions on the map on the display panel to the driver.

The selection condition generating unit 23 sets a data selection condition C3 on the basis of position and dimension of the detecting object detected by the object detector 31 so that the reconfigured spectrum data E1 to En does not contain information about a part corresponding to the current position of the detecting object. Further, the selection condition generating unit 23 may generate the data selection condition C3 on the basis of the priority of the measuring object. For example, the selection condition generating unit 23 may add a condition that the current position of the detecting object is not selected to the previously generated data selection condition C2 to generate the data selection condition C3. The data selection condition C3 may be generated from the data selection condition C2 and the condition that the current position of the detecting object is not selected.

The selection condition generating unit 23 sets the data selection condition C3 thus generated to the data transfer device 15. The data transfer device 15 generates the reconfigured spectrum data E1 to En from the measured spectrum data D1 to Dm on the basis of the set data selection condition C3. Thus, the amount of the reconfigured spectrum data E1 to En is reliably reduced from the amount of the measured spectrum data D1 to Dm. The data transfer device 15 may process the data selection condition C2 and then, the data selection condition C3, or may process the data selection condition C3 at the same time.

In this manner, the fifth embodiment in FIG. 9 can also obtain the same or similar advantages as those in the first and third embodiments as well as a following advantage.

(12) The data transfer device 15 eliminates the spectrum data corresponding to the measuring object already detected by the object detector 31 such as the map information and the radar from the reconfigured spectrum data E1 to En. Thus, an unnecessary portion of the amount of the reconfigured spectrum data E1 to En is reliably reduced.

Each of the above-mentioned embodiments can be implemented in the following modes.

Figure 10:
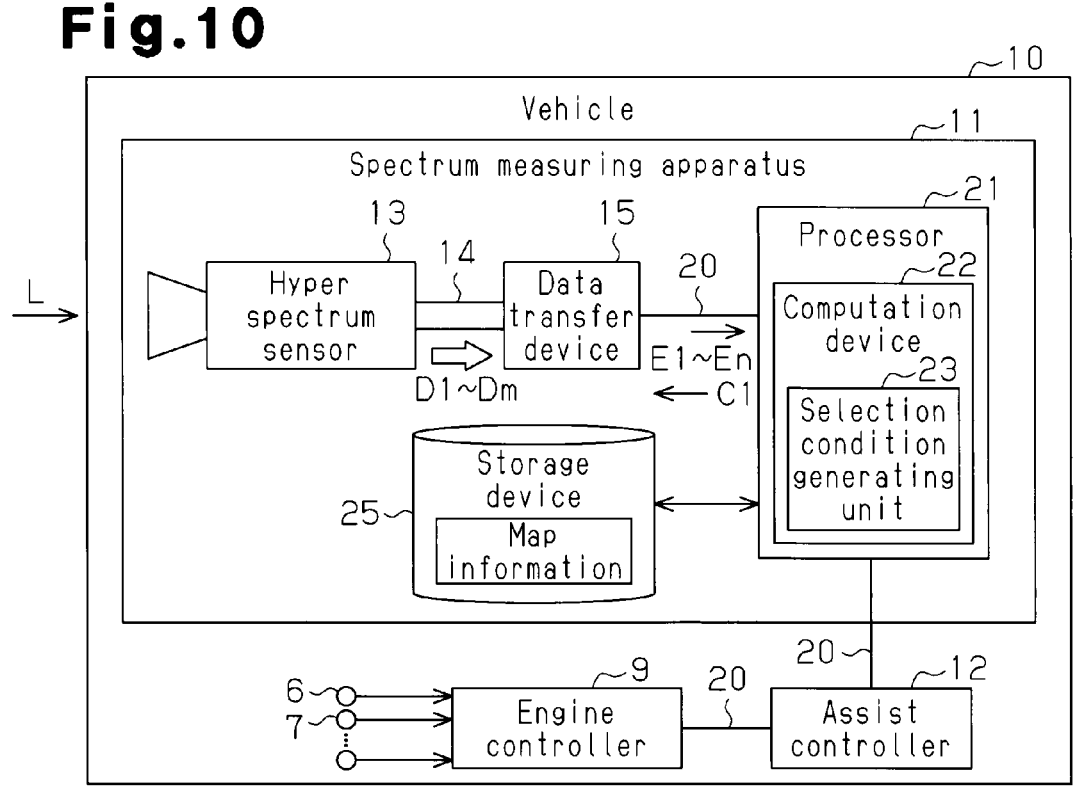
FIG. 10 is a block diagram showing schematic configuration of a movable body spectrum measuring apparatus in a modification of the present invention.

As shown in FIG. 10, the map information may be stored in the storage device 25 of the spectrum measuring apparatus 11. That is, the map information is not necessarily stored in the navigation device 30 and the object detector 31, which are external to the spectrum measuring apparatus 11, as in the third and fourth embodiments.

Figure 11:
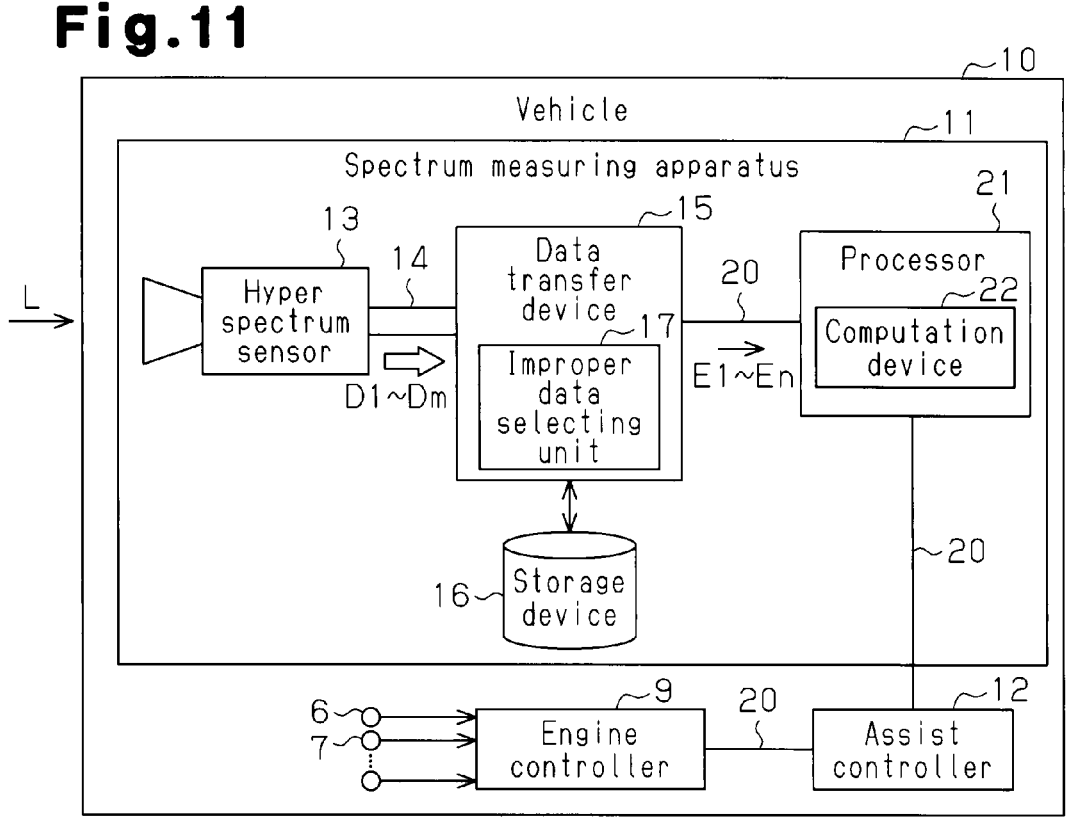
FIG. 11 is a block diagram showing schematic configuration of a movable body spectrum measuring apparatus in another modification of the present invention.

As shown in FIG. 11, the data transfer device 15 in each of the above-mentioned embodiments may have an improper data selecting unit 17. The improper data selecting unit 17 prevents insignificant information from being included in the reconfigured spectrum data E1 to En by eliminating insignificant information contained in the measured spectrum data D1 to Dm. By examining the optical intensity information contained in the measured spectrum data D1 to Dm, the improper data selecting unit 17 detects the optical intensity information having, for example, a saturated value exceeding the upper limit value or a lower limit value or an unchanged value that is equal to or smaller than the lower limit value, as the insignificant optical intensity information. The data transfer device 15 does not select the optical intensity information detected as improper data as the reconfigured spectrum data E1 to En, that is, eliminates the optical intensity information detected as improper data. Thus, the amount of data transferred as the reconfigured spectrum data E1 to En can be reduced. Moreover, by preventing the insignificant optical intensity information from being contained in the reconfigured spectrum data E1 to En, the recognition accuracy of the measuring apparatus can be maintained. After that, the improper data selecting unit 17 may be applied to the reconfigured spectrum data E1 to En generated from the measured spectrum data D1 to Dm on the basis of the data selection conditions.

Figure 12:
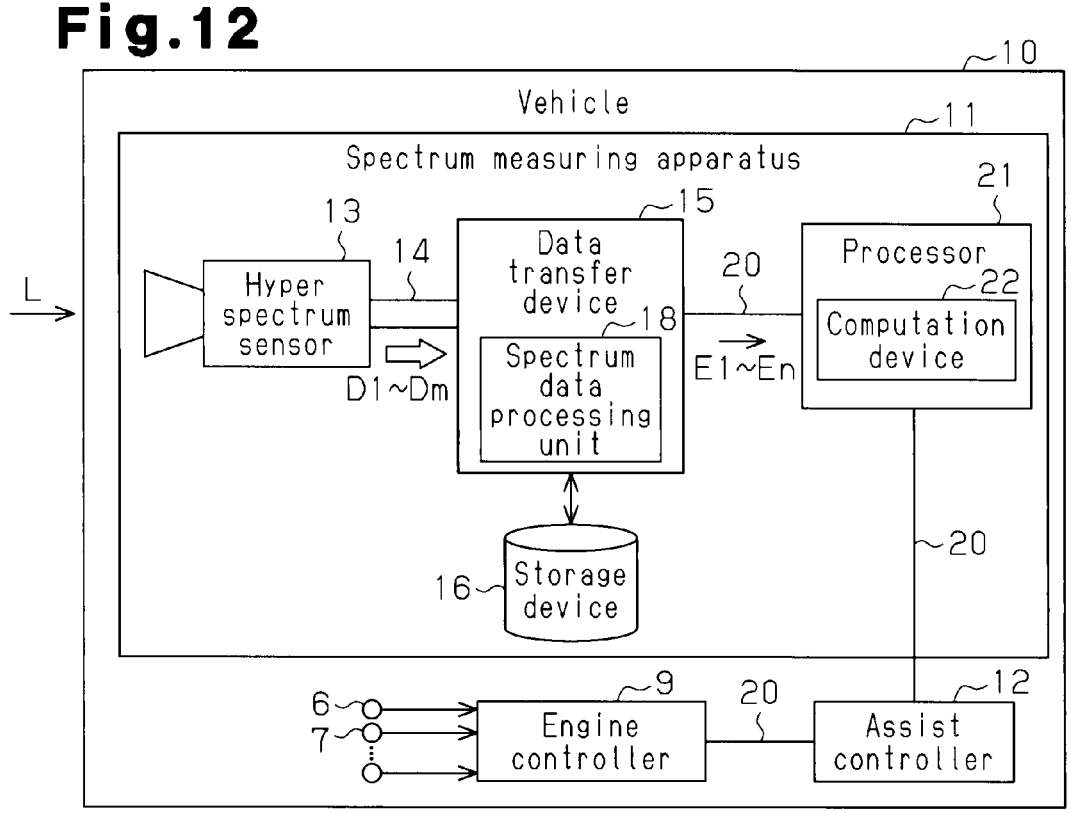
FIG. 12 is a block diagram showing schematic configuration of a movable body spectrum measuring apparatus in still another modification of the present invention.

As shown in FIG. 12, the data transfer device 15 may have a spectrum data processing unit 18 for processing a part of the measured spectrum data D1 to Dm. The spectrum data processing unit 18 reduces the wavelength information on the basis of the data selection condition C1. For example, the spectrum data processing unit 18 averages or convolves the optical intensity information in a certain wavelength range set as a range that does not vary information so much and thus, has a small impact on recognition of the measuring object, for example, the range of 550 nm to 650 nm. That is, the spectrum data processing unit 18 obtains representative optical intensity information corresponding to one certain representative wavelength, for example, 600 nm.

Thus, a plurality of pieces of wavelength information of continuous wavelengths and a plurality of pieces of optical intensity information corresponding to the wavelength information are each replaced with one piece of wavelength information and one piece of optical intensity information corresponding to the one piece of wavelength information. For this reason, the amount of the reconfigured spectrum data E1 to En is reduced in due course. For example, the data transfer device 15 replaces the plurality of pieces of wavelength information corresponding to the wavelength range of 550 nm to 650 nm with the wavelength information of 600 nm, and calculates the optical intensity information corresponding to the wavelength range of 550 nm to 650 nm as the optical intensity information corresponding to the wavelength information of 600 nm by convolution or averaging. Thus, the wavelength information of 550 nm to 650 nm and the optical intensity information corresponding to the wavelength information are selected as the wavelength information of 600 nm and the optical intensity information corresponding to the wavelength information.

Figure 13:
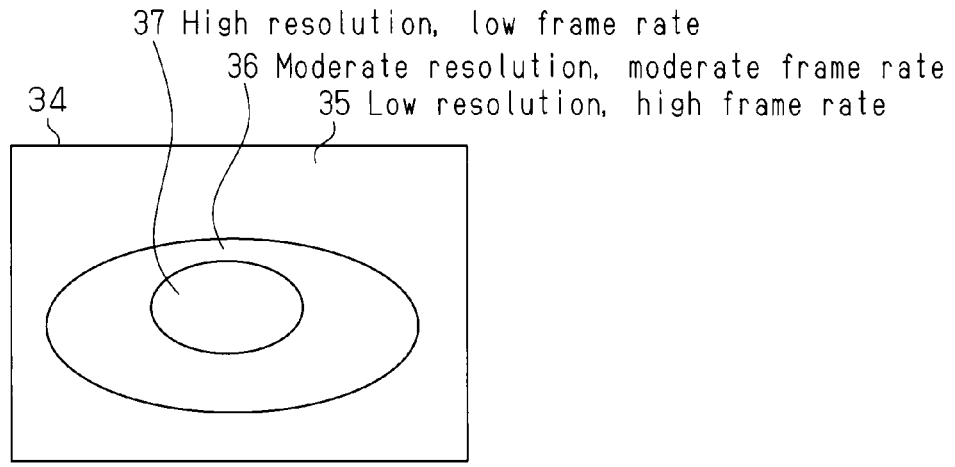
FIG. 13 is a schematic view showing conditions for selecting information contained in the spectrum data by a movable body spectrum measuring apparatus in still another modification of the present invention.

As shown in FIG. 13, the selection condition generating unit 23 in the third to fifth embodiments may change the reconfigured frame rate n, the number of reconfigured bands y and the reconfigured resolution, that is, the reconfigured resolution g×h according to each of a peripheral region 35 as a peripheral part, a transition region 36 as a middle part and a central region 37 as a central part in a spectrum image 34.

Generally, in the spectrum image 34 such as the single-wavelength images F1 to Fx, a measuring object in the peripheral region 35 looks large since the relative distance with respect to the vehicle 10 is small, and the relative speed with respect to the vehicle 10, that is, the moving speed on the spectrum image 34 is high. For this reason, as the data selection conditions for the peripheral region 35 in the spectrum image 34, a low reconfigured resolution g×h or the small number of reconfigured bands y is set in place of increasing the reconfigured frame rate n so that the processor 21 can rapidly recognize the measuring object. In contrast, a measuring object in the central region 37 in the spectrum image 34 looks small since the relative distance with respect to the vehicle 10 is large, and the relative speed with respect to the vehicle 10, that is, the moving speed on the spectrum image 34 is low. For this reason, as the data selection conditions for the central region 37 in the spectrum image 34, a low reconfigured frame rate n is set in place of setting a high reconfigured resolution g×h or the large number of reconfigured bands y so that the processor 21 can recognize the measuring object with high accuracy. For the transition region 36 located between the peripheral region 35 and the central region 37 in the spectrum image 34, as the data selection conditions, a moderate reconfigured resolution g×h, the moderate number of reconfigured bands y and a moderate reconfigured frame rate n are set.

Thus, to generate the reconfigured spectrum data E1 to En, the data transfer device 15 can change the wavelength interval, that is, the wavelength resolution of the wavelength information, the density, that is, the resolution of the optical intensity information, and the acquisition time interval, that is, the frame rate of the measured spectrum data according to the vehicle speed V and the state of the vehicle 10 by the steering operation. Thus, the spectrum measuring apparatus can recognize a measuring object on the basis of the appropriate reconfigured spectrum data E1 to En reconfigured according to the movable body state. In turn, the measuring object can be discriminated more reliably. For example, as compared to the case where information is selected by using the same conditions for all regions in the spectrum image, the amount of the reconfigured spectrum data can be reduced while keeping the recognition accuracy of the measuring object. Thus, the recognition processing of the measuring object can be easily achieved in real time.

Also in the first or second embodiment, the data selection conditions can be set in the data transfer device 15 and the storage device 16 by changing the reconfigured frame rate n, the number of reconfigured bands y and the reconfigured resolution g×h according to each of the peripheral region 35, the transition region 36 and the central region 37 in spectrum image 34.

The selection condition generating unit 23 in the third to fifth embodiments may set the reconfigured frame rate n in the region corresponding to a new moving direction in the spectrum image 34 to be large according to the steering operational angle, that is, the steering angle. That is, the reconfigured resolution g×h and the number of reconfigured bands y may be set small in place of rapidly recognizing the measuring object. Thus, the processor 21 can reliably recognize the measuring object in the new movement direction in real time.

Figure 14:
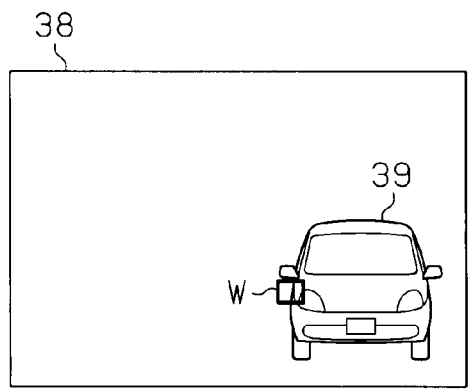
FIG. 14 is a schematic view showing conditions for selecting information contained in the spectrum data by a movable body spectrum measuring apparatus in still another modification of the present invention.

As shown in FIG. 14, when a measuring object 39 is recognized in a spectrum image 38, the selection condition generating unit 23 in the third to fifth embodiments may set a weighted frame W at a boundary between the measuring object 39 and background. The data selection conditions may be generated by changing the reconfigured frame rate n, the reconfigured resolution g×h and the number of reconfigured bands y for this weighted frame W. For example, in order to rapidly recognize a face or the like of a pedestrian as the measuring object 39 appearing from behind another vehicle as a blind spot, the weighted frame W is set so as to previously lock on the face or the like of the pedestrian. That is, a high reconfigured frame rate n is set to the weighted frame W, and since the weighted frame W is small, the reconfigured resolution g×h and the number of reconfigured bands y are also set high. Thus, the further measuring object appearing from the blind spot of the measuring object 39 can be rapidly detected in the recognition processing in real time without greatly increasing the amount of the reconfigured spectrum data E1 to En.

In the first embodiment, the data transfer device 15 acquires the data selection conditions from the storage device 16 to generate the reconfigured spectrum data E1 to En that does not exceed the transfer maximum value. The present invention is not limited to this, and when the data selection conditions has the priority of the measuring object, the data transfer device may successively select information about the measuring object with high priority so that the reconfigured spectrum data E1 to En does not exceed the transfer maximum value. For example, when the reconfigured spectrum data E1 to En is generated without considering the priority and the amount of the reconfigured spectrum data E1 to En exceeds the transfer maximum value, the data transfer device 15 recreates the reconfigured spectrum data E1 to En so as to select only information about the measuring object with high priority.

In the second embodiment, the new reconfigured resolution g1×h1 is not necessarily maintained to the initial reconfigured resolution g0×h1 and may be changed. For example, both the new reconfigured resolution g1×h1 and the new number of reconfigured bands y1 are changed. Thus, the flexibility in setting the data selection conditions is improved.

In the second embodiment, the speed table 19 does not necessarily associate the reconfigured frame rate n with the vehicle speed V, and may associate the reconfigured frame rate n with the set steering angle of the vehicle. For example, in order to find the measuring object within a short time, as the steering angle increases, the reconfigured frame rate n is increased and the number of reconfigured bands y is decreased. Thus, it is possible to reliably set the reconfigured frame rate n according to the state of the vehicle.

In the first and second embodiments, the storage device 16 may store data containing the wavelength information necessary for recognizing the measuring object therein. Thus, the data transfer device may generate the reconfigured spectrum data containing the wavelength information necessary for the measuring object by acquiring data corresponding to the measuring object. As a result, the spectrum measuring apparatus 11 can reduce the data amount and improve recognition accuracy for the selected measuring object.

In the first and second embodiments, the storage device 16 may store data of the wavelength information included in the light source. That is, the data transfer device 15 can generate the reconfigured spectrum data E1 to En so as to reliably contain the wavelength information included in the light source.

In the first embodiment, among the reconfigured frame rate n, the reconfigured resolution g×h and the number of reconfigured bands y, a plurality of conditions may be simultaneously selected or only one may be set. The flexibility in designing the spectrum measuring apparatus 11 is improved. For example, when the amount of the measured spectrum data D1 to Dm is small, information may be selected according to effective conditions.

In the first embodiment, the reconfigured frame rate n, the reconfigured resolution g×h and the number of reconfigured bands y are not necessarily predetermined and may be optionally changed by a setting device. For example, the data transfer device 15 and the processor 21 may change the selected information according to a change in the amount of other data passing through the on-vehicle network 20. Another device may change the selected information. The flexibility in selecting the data selection conditions is thus improved.

The data selection conditions may be set according to an arithmetic expression, not a map. The flexibility in designing the data selection conditions in the spectrum measuring apparatus 11 is therefore improved.

Figure 15:
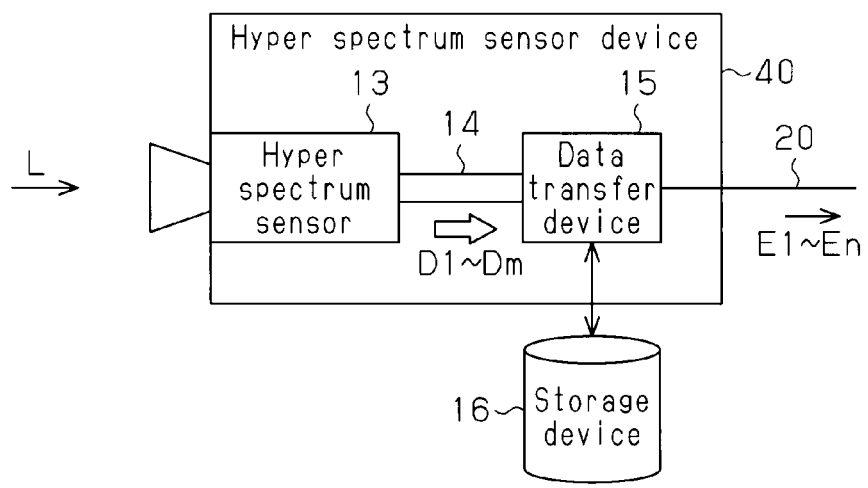
FIG. 15 is a block diagram showing schematic configuration of a movable body spectrum measuring apparatus in still another modification of the present invention.

As shown in FIG. 15, the hyper spectrum sensor 13 and the data transfer device 15 may be unitized to constitute one hyper spectrum sensor device 40. The hyper spectrum sensor device 40 has a bus constituting the large-capacity communication circuit 14 for connecting the hyper spectrum sensor 13 to the data transfer device 15. In this case, the spectrum measuring apparatus 11 can be miniaturized.

In each of the above-mentioned embodiments, the selected information as the data selection conditions constitutes the reconfigured spectrum data E1 to En. However, the present invention is not limited to this. Conversely, information as the data selection conditions, which does not constitute the reconfigured spectrum data E1 to En, may be set. Also in this case, the flexibility in setting the data selection condition is improved.

In each of the above-mentioned embodiments, the on-vehicle network 20 is CAN. However, the on-vehicle network 20 is not limited to the CAN and may be other network such as Ethernet (registered trademark), FlexRay (registered trademark) and IEEE1394 (FireWire (registered trademark)) as long as it enables network communication. Thereby, the adoptability of the spectrum measuring apparatus is increased.

DESCRIPTION OF THE REFERENCE NUMERALS

10 . . . Vehicle, 11 . . . Spectrum Measuring Apparatus, 12 . . . Assist Controller, 13 . . . Hyper Spectrum Sensor, 14 . . . Large-Capacity Communication Circuit, 15 . . . Data Transfer Device, 16 . . . Storage Device, 17 . . . Improper Data Selecting Unit, 18 . . . Spectrum Data Processing Unit, 19 . . . Speed Table, 20 . . . On-Vehicle Network, 21 . . . Processor, 22 . . . Computation Device, 23 . . . Selection Condition Generating Unit, 25 . . . Storage Device, 30 . . .

Navigation Device, 31 . . . Object Detector, 34 . . . Spectrum Image, 35 . . . Peripheral Region, 36 . . . Transition Region, 37 . . . Central Region, 38 . . . Spectrum Image, 39 . . . Measuring Object, 40 . . . Hyper Spectrum Sensor Device, D . . . Measured Spectrum Data, E . . . Reconfigured Spectrum Data, F . . . Single-Wavelength Image, G . . . Reconfigured Single-Wavelength Image, L . . . Observation Light, P, Q . . . Pixel.

The invention claimed is:

1. A movable body spectrum measuring apparatus comprising:
a spectrum sensor mounted in a movable body to measure spectrum data containing information including wavelength information and optical intensity information of a measuring object;
processor circuitry mounted in the movable body to discriminate the measuring object by processing reconfigured spectrum data; and
a signal transmission path configured to transmit the measured spectrum data from the spectrum sensor to data transfer device circuitry, and configured to transfer the reconfigured spectrum data from the data transfer device circuitry to the processor circuitry, and
the data transfer device circuitry configured to select information from the measured spectrum data to acquire the reconfigured spectrum data,
wherein the data transfer device circuitry is configured to transfer the reconfigured spectrum data to the processor circuitry through the signal transmission path,
wherein the data transfer device circuitry is configured to select a part of the wavelength information contained in the measured spectrum data to acquire the reconfigured spectrum data,
wherein the data transfer device circuitry is configured to select the wavelength information contained in ambient light in surroundings around the movable body to acquire the reconfigured spectrum data.

2. The movable body spectrum measuring apparatus according to claim 1, wherein the data transfer device circuitry is configured to select the wavelength information necessary for discrimination of the measuring object to acquire the reconfigured spectrum data.

3. The movable body spectrum measuring apparatus according to claim 1, wherein the data transfer device circuitry acquires the reconfigured spectrum data by extracting and excluding wavelength information having insignificant optical intensity information from information contained in the measured spectrum data.

4. The movable body spectrum measuring apparatus according to claim 1, wherein
the movable body includes a movable body state acquiring unit configured to acquire a movable body state as a state of the movable body, and
the data transfer device circuitry is configured to determine the selected information according to the movable body state to acquire the reconfigured spectrum data.

5. The movable body spectrum measuring apparatus according to claim 1, wherein
the processor circuitry is configured to set the selected information,
the processor circuitry is configured to make a request to the data transfer device circuitry on the basis of a recognition result of the measuring object, and
the data transfer device circuitry is configured to determine the selected information according to the request to acquire the reconfigured spectrum data.

6. The movable body spectrum measuring apparatus according to claim 5, wherein
there are a plurality of measuring objects including an object of high occurrence ratio having a higher occurrence ratio than a rest of one or more other measuring objects among the plurality of measuring objects,
data amount reduced by reconfiguration from the measured spectrum data to the reconfigured spectrum data is referred to as data reduced amount, and
the processor circuitry is configured to set the selected information such that the data reduced amount of the object of high occurrence ratio is smaller than that of the other measuring objects.

7. The movable body spectrum measuring apparatus according to claim 1, wherein
the measured spectrum data is used to generate a spectrum image, and
the data transfer device circuitry is configured to select the selected information corresponding to a central region of the spectrum image to be different from the selected information corresponding to a peripheral region of the spectrum image.

8. The movable body spectrum measuring apparatus according to claim 1, wherein
the processor circuitry is configured to set the selected information,
a specified one of the measuring object is referred to as a specific measuring object, and
when recognizing that the specific measuring object exists in a measuring scope of the spectrum sensor, the processor circuitry is configured to set the selected information so as to exclude the measured spectrum data corresponding to the existence of the specific measuring object.

9. The movable body spectrum measuring apparatus according to claim 1, wherein
in order to generate the reconfigured spectrum data, the data transfer device circuitry
represents the wavelength information corresponding to wavelength in a certain range as representative wavelength information, and
calculates representative optical intensity information on the basis of optical intensity information corresponding to the wavelength information.

10. A movable body spectrum measuring apparatus comprising:
a spectrum sensor mounted in a movable body to measure spectrum data containing information including wavelength information and optical intensity information of a measuring object;
processor circuitry mounted in the movable body to discriminate the measuring object by processing reconfigured spectrum data; and
a signal transmission path configured to transmit the measured spectrum data from the spectrum sensor to data transfer device circuitry, and configured to transmit the reconfigured spectrum data from the data transfer device circuitry to the processor circuitry, and
the data transfer device circuitry configured to select information from the measured spectrum data to acquire the reconfigured spectrum data,
wherein the data transfer device circuitry is configured to transfer the reconfigured spectrum data to the processor circuitry through the signal transmission path,
wherein the data transfer device circuitry is configured to select a part of the optical intensity information contained in the measured spectrum data to acquire the reconfigured spectrum data, the data transfer device circuitry is configured to set a transfer maximum value as a maximum value of data amount transferable to the processor circuitry, and the data transfer device circuitry is configured to limit the amount of selected information such that the amount of the reconfigured spectrum data is equal to or smaller than the transfer maximum value.

11. A movable body spectrum measuring apparatus comprising:

a spectrum sensor mounted in a movable body to measure spectrum data containing information including wavelength information and optical intensity information of a measuring object;

processor circuitry mounted in the movable body to discriminate the measuring object by processing reconfigured spectrum data; and a signal transmission path configured to transmit the measured spectrum data from the spectrum sensor to data transfer device circuitry, and configured to transmit the reconfigured spectrum data from the data transfer device circuitry to the processor circuitry, and the data transfer device circuitry configured to select information from the measured spectrum data to acquire the reconfigured spectrum data, wherein the data transfer device circuitry is configured to transfer the reconfigured spectrum data to the processor circuitry through the signal transmission path, wherein the measured spectrum data corresponds to each of a plurality of spectrum images over time, and the data transfer device circuitry is configured to select information about the measured spectrum data corresponding to a partial period in a plurality of pieces of the measured spectrum data to acquire the reconfigured spectrum data.

12. A movable body spectrum measuring apparatus comprising:

a spectrum sensor mounted in a movable body to measure spectrum data containing information including wavelength information and optical intensity information of a measuring object;

processor circuitry mounted in the movable body to discriminate the measuring object by processing reconfigured spectrum data; and a signal transmission path configured to transmit the measured spectrum data from the spectrum sensor to data transfer device circuitry, and configured to transmit the reconfigured spectrum data from the data transfer device circuitry to the processor circuitry, and the data transfer device circuitry configured to select information from the measured spectrum data to acquire the reconfigured spectrum data, wherein the data transfer device circuitry is configured to transfer the reconfigured spectrum data to the processor circuitry through the signal transmission path, wherein the data transfer device circuitry is configured to set a transfer maximum value as a maximum value of data amount transferable to the processor circuitry, and the data transfer device circuitry is configured to limit the amount of selected information such that the amount of the reconfigured spectrum data is equal to or smaller than the transfer maximum value, wherein priority is set to each of a plurality of the measuring objects, and the data transfer device circuitry is configured to determine the selected information on the basis of the priority to acquire the reconfigured spectrum data.

13. A movable body spectrum measuring method comprising:

measuring spectrum data containing information including wavelength information and optical intensity information of a measuring object by a spectrum sensor mounted in a movable body;

discriminating the measuring object by processing reconfigured spectrum data by processor circuitry mounted in the movable body;

transmitting the measured spectrum data from the spectrum sensor to data transfer device circuitry via a signal transmission path, acquiring the reconfigured spectrum data by selecting information from the measured spectrum data; and transferring the reconfigured spectrum data to the processor circuitry via the signal transmission path, wherein selecting the information by the data transfer device circuitry includes:

selecting a part of the wavelength information contained in the measured spectrum data to acquire the reconfigured spectrum data; and selecting the wavelength information contained in ambient light in surroundings around the movable body to acquire the reconfigured spectrum data.

* * * * *